US010391105B2

(12) United States Patent
Cashman et al.

(10) Patent No.: US 10,391,105 B2
(45) Date of Patent: Aug. 27, 2019

(54) METHODS OF TREATING CERTAIN DEPRESSIVE DISORDERS AND DELIRIUM TREMENS

(71) Applicant: Marinus Pharmaceuticals Inc., Radnor, PA (US)

(72) Inventors: Christopher Cashman, Radnor, PA (US); Jaakko Lappalainen, Radnor, PA (US); David A Czekai, Radnor, PA (US)

(73) Assignee: MARINUS PHARMACEUTICALS INC., Radnor, PA (US)

( * ) Notice: Subject to any disclaimer, the term of this patent is extended or adjusted under 35 U.S.C. 154(b) by 0 days.

(21) Appl. No.: 15/700,314

(22) Filed: Sep. 11, 2017

(65) Prior Publication Data
US 2018/0071315 A1 Mar. 15, 2018

Related U.S. Application Data

(60) Provisional application No. 62/385,539, filed on Sep. 9, 2016.

(51) Int. Cl.
*A61K 31/56* (2006.01)
*A61K 31/573* (2006.01)
*C07J 7/00* (2006.01)
*A61K 31/721* (2006.01)
*A61K 31/718* (2006.01)

(52) U.S. Cl.
CPC ............. *A61K 31/573* (2013.01); *C07J 7/009* (2013.01); *A61K 31/718* (2013.01); *A61K 31/721* (2013.01)

(58) Field of Classification Search
CPC .............................. A61K 31/57; A61K 31/565
USPC .................... 514/169, 170, 177, 182
See application file for complete search history.

(56) References Cited

U.S. PATENT DOCUMENTS

| | | |
|---|---|---|
| 4,540,602 A | 9/1985 | Motoyama et al. |
| 4,783,484 A | 11/1988 | Violante et al. |
| 4,826,689 A | 5/1989 | Violanto et al. |
| 4,997,454 A | 3/1991 | Violante et al. |
| 5,134,127 A | 7/1992 | Stella et al. |
| 5,145,684 A | 9/1992 | Liversidge et al. |
| 5,298,262 A | 3/1994 | Na et al. |
| 5,314,217 A | 5/1994 | Place |
| 5,346,702 A | 9/1994 | Na et al. |
| 5,352,459 A | 10/1994 | Hollister et al. |
| 5,376,645 A | 12/1994 | Stella et al. |
| 5,399,363 A | 3/1995 | Liversidge et al. |
| 5,429,824 A | 7/1995 | June |
| 5,470,583 A | 11/1995 | Na et al. |
| 5,494,683 A | 2/1996 | Liversidge et al. |
| 5,518,187 A | 5/1996 | Bruno et al. |
| 5,534,270 A | 7/1996 | De Castro |
| 5,543,133 A | 8/1996 | Swanson et al. |
| 5,560,932 A | 10/1996 | Bagchi et al. |
| 5,662,883 A | 9/1997 | Bagchi et al. |
| 5,665,331 A | 9/1997 | Bagchi et al. |
| 5,718,388 A | 2/1998 | Czekai et al. |
| 5,741,522 A | 4/1998 | Violante et al. |
| 5,776,496 A | 7/1998 | Violante et al. |
| 5,862,999 A | 1/1999 | Czekai et al. |
| 6,228,398 B1 | 5/2001 | Devane et al. |
| 6,248,363 B1 | 6/2001 | Patel et al. |
| 6,264,922 B1 | 7/2001 | Wood et al. |
| 6,267,989 B1 | 7/2001 | Liversidge et al. |
| 6,375,986 B1 | 4/2002 | Ryde et al. |
| 6,428,814 B1 | 8/2002 | Bosch et al. |
| 6,569,463 B2 | 5/2003 | Patel et al. |
| 6,592,903 B2 | 7/2003 | Ryde et al. |
| 6,689,378 B1 | 2/2004 | Sun et al. |
| 6,730,325 B2 | 5/2004 | Devane et al. |
| 6,923,988 B2 | 8/2005 | Patel et al. |

(Continued)

FOREIGN PATENT DOCUMENTS

| | | |
|---|---|---|
| EP | 0169618 | 1/1986 |
| EP | 0498824 A1 | 8/1992 |

(Continued)

OTHER PUBLICATIONS

Nohria et al.; "Ganaxolone"; The Journal of the American Society for Experimental NeuroTherapeutics; 4; pp. 102-105; (2007).
Akers, "Excipient—Drug Interactions in Parenteral Formulations," Journal of Pharmaceutical Sciences, vol. 91, No. 1, Nov. 11, 2002, pp. 2283-2300.
Liptakova, el al. "Effect of Ganaxolone on Flurothyl Seizures in Developing Rats," Epilepsia, 41 (7), pp. 788-793, (2000).
Aiken el al., "Treatment of Epilepsy: Existing Therapies and Future Developments," Frontiers in Bioscience 5; Nov. 1, 2000, pp. 124-152.
Botella et al., "Neuroactive Steriods. 1. Positive Allosteric Modulators of the (γ-Aminobutyric Acid) A Receptor: Structure-Activity Relationships of Heterocylic Substitution at C-21," American Chemical Society, (2015), pp. 3500-3511.

(Continued)

Primary Examiner — Raymond J Henley, III
(74) Attorney, Agent, or Firm — Cantor Colburn LLP

(57) ABSTRACT

The disclosure provides a method of treating a patient having postpartum depression, premenstrual dysphoric disorder, menopausal depression, or delirium tremens comprising administering an effective amount of an injectable neurosteroid formulation to the patient. In certain embodiments the injectable neurosteroid formulation is an injectable ganaxolone formulation. Two types of injectable neurosteroid formulations may be used in the disclosed methods. The first such formulation is an injectable formulation containing ganaxolone and sulfobutyl ether β-cyclodextrin in a 1:1 inclusion complex. The second such formulation is an injectable neurossteroid formulation comprising a neurosteroid, preferably ganaxolone, but which may be a neurosteroid selected from allopregnanolone, ganaxolone, alphaxalone, alphadolone, hydroxydione, minaxolone, pregnanolone, tetrahydrocorticosterone, and combinations of the foregoing; a surface stabilizer selected from hydroxyl ethyl starch, dextran, and povidone; and a surfactant.

14 Claims, No Drawings

(56) References Cited

U.S. PATENT DOCUMENTS

| | | |
|---|---|---|
| 6,969,529 B2 | 11/2005 | Bosch et al. |
| 6,976,647 B2 | 12/2005 | Reed et al. |
| 7,078,057 B2 | 7/2006 | Kerkhof |
| 7,198,795 B2 | 4/2007 | Cooper et al. |
| 7,550,445 B2 | 6/2009 | Nerurkar et al. |
| 7,858,609 B2 | 12/2010 | Shaw et al. |
| 8,003,127 B2 | 8/2011 | Liversidge et al. |
| 8,022,054 B2 | 9/2011 | Shaw et al. |
| 8,318,714 B2 | 11/2012 | Shaw et al. |
| 8,362,286 B2 | 1/2013 | Shaw et al. |
| 8,367,651 B2 | 2/2013 | Shaw et al. |
| 8,455,002 B2 | 6/2013 | Shaw et al. |
| 8,604,011 B2 | 12/2013 | Mellon |
| 8,618,087 B2 | 12/2013 | Shaw et al. |
| 8,658,692 B2 | 2/2014 | Kim et al. |
| 9,017,728 B2 | 4/2015 | Shaw et al. |
| 9,029,355 B2 | 5/2015 | Shaw et al. |
| 9,056,116 B2 | 6/2015 | Shaw et al. |
| 9,452,176 B2 | 9/2016 | Shaw et al. |
| 2002/0012675 A1 | 1/2002 | Jain et al. |
| 2002/0150616 A1 | 10/2002 | Vandecruys |
| 2003/0054042 A1 | 3/2003 | Liversidge et al. |
| 2003/0129242 A1 | 7/2003 | Bosch et al. |
| 2004/0105889 A1 | 6/2004 | Ryde et al. |
| 2004/0214746 A1 | 10/2004 | Bosch et al. |
| 2004/0258757 A1 | 12/2004 | Bosch et al. |
| 2005/0031691 A1 | 2/2005 | McGurk et al. |
| 2005/0181050 A1 | 8/2005 | Hirsh et al. |
| 2006/0216353 A1 | 9/2006 | Liversidge et al. |
| 2007/0141161 A1 | 6/2007 | Shaw et al. |
| 2009/0004262 A1 | 1/2009 | Shaw et al. |
| 2011/0236487 A1 | 9/2011 | Shaw et al. |
| 2012/0052098 A1 | 3/2012 | Shaw et al. |
| 2014/0057885 A1 | 2/2014 | Reddy et al. |
| 2014/0249120 A1 | 11/2014 | Covey et al. |
| 2014/0343027 A1 | 11/2014 | Rogawski |
| 2015/0018327 A1 | 1/2015 | Reddy |
| 2015/0158903 A1 | 6/2015 | Upasani et al. |
| 2015/0290181 A1* | 10/2015 | Lee .................. A61K 8/41 424/771 |
| 2015/0313915 A1* | 11/2015 | Rogawski .......... A61K 47/40 514/182 |
| 2015/0361125 A1 | 12/2015 | Covey |
| 2016/0022701 A1 | 1/2016 | Reddy et al. |
| 2016/0031930 A1 | 2/2016 | Botella et al. |
| 2016/0068563 A1 | 3/2016 | Botella et al. |
| 2016/0083417 A1 | 3/2016 | Botella et al. |
| 2016/0083418 A1 | 3/2016 | Botella et al. |
| 2016/0108080 A1 | 4/2016 | Botella et al. |
| 2016/0152658 A1 | 6/2016 | Botella et al. |
| 2016/0228454 A1 | 8/2016 | Zhang et al. |
| 2017/0202855 A1* | 7/2017 | Shaw .................. A61K 31/573 |
| 2017/0233432 A1 | 8/2017 | Botella et al. |
| 2017/0258812 A1 | 9/2017 | Zhang et al. |
| 2017/0305960 A1 | 10/2017 | Botella et al. |
| 2018/0051052 A1 | 2/2018 | Martinez Botella et al. |

FOREIGN PATENT DOCUMENTS

| | | |
|---|---|---|
| EP | 0499299 A2 | 8/1992 |
| EP | 0580690 A1 | 2/1994 |
| WO | 200145674 A1 | 6/2001 |
| WO | 200145677 A1 | 6/2001 |
| WO | 2011088503 A1 | 7/2011 |
| WO | 2014085668 A1 | 6/2014 |
| WO | 2014127201 A1 | 8/2014 |
| WO | 2014160441 A1 | 10/2014 |
| WO | 2014160480 A1 | 10/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |

OTHER PUBLICATIONS

Loftsson et al., "Cyclodextrins in Drug Delivery," Expert Opinion Drug Delivery (2005), 2(2) pp. 335-351.

Lyden et al., "Effect of Ganaxolone in a Rodent Model of Cerebral Hematoma," Stroke, Jan. 2000, pp. 169-175.

Marinus Pharmaceuticals, "Marinus Pharmaceuticals, Inc. Enters Into Use Agreement with CyDex Pharmaceuticals, Inc. for use of Captisol (R) for Ganaxolone IV," (Aug. 12, 2014), XP-002756531, retrieved from the internet, 3 pages.

Monaghan et al., "Initial Human Experience with Ganaxolone, a Neuroactive Steroid with Antiepileptic Activity," Epilepsia, vol. 38, No. 9, (1997), pp. 1026-1031.

Moyne el al., "Sterilization of Injectable Drugs Solutions by Irradiation," Radiation Physics and Chemistry 63 (2002), pp. 703-704.

Mula, "Emerging Drugs for Focal Epilepsy," XP-002756532 Expert Opinion, (2013) 18 (1): pp. 87-95.

Pieribone et al., "Clinical Evaluation of Ganaxolone in Pediatric and Adolescent Patients With Refractory Epilepsy," Epilepsia, vol. 48, No. 10, (2007), pp. 1870-1874.

Pramanick et al., "Excipient Selection in Parenteral Formulation Development," Pharma Times, vol. 45, No. 3, Mar. 2013, pp. 65-77.

Rogawski et al., "Neuroactive Steroids for the Treatment of Status Epilepticus," Epilepsia, 54 (Suppl. 6), (2013), pp. 93-98.

Wong et al., "Suspensions for Intravenous (IV) Injection: A Review of Development, Preclinical and Clinical Aspects," Advanced Drug Delivery Reviews 60 (2008) pp. 939-954.

* cited by examiner

METHODS OF TREATING CERTAIN DEPRESSIVE DISORDERS AND DELIRIUM TREMENS

CROSS REFERENCE TO RELATED APPLICATION

The application claims priority from U.S. Provisional Application No. 62/385,539 filed Sep. 9, 2016, which is hereby incorporated by reference in its entirety.

BACKGROUND

Postpartum depression is a mood disorder that occurs in some women following the birth of a child. Common symptoms include feelings of extreme sadness, loneliness, anxiety, and exhaustion, and mirror those of Major Depressive Disorder with the additional criteria that the onset of symptoms begins within 4 weeks of childbirth. In some cases sufferers can develop psychosis. Rapidly declining postpartum progesterone and allopregnanolone levels are thought to contribute to the development of postpartum depression. The CDC estimates between 10-15% of mothers experience postpartum depression within a year of giving birth, with approximately 7% of women experiencing postpartum depression within three months of delivery. The rates are likely higher in developing countries. Few women, likely less than 15% seek medical treatment for the symptoms of postpartum depression. When treated, the most commonly used medications are Selective Serotonin Reuptake Inhibitors (SSRI's) and Serotonin-norepinephrine Reuptake Inhibitors (SNRI' s), medications than require several weeks to take effect. Allopregnanolone has previously been administered as an intravenous infusion to women suffering from postpartum depression, and found to be strongly efficacious in placebo-controlled studies. All women in the study were suffering from postpartum depression and exhibited a Hamilton Depression Rating Scale (HAM-D) baseline score of greater than 25. At the end of a sixty hour infusion patients has a mean HAM-D score 12 points lower than placebo-treated subjects. The 12 point difference in HAM-D score from placebo is larger than the typical 3 to 5 point difference observed in clinical studies for other antidepressants. Allopregnanolone's effects were also found to be long lasting, persisting 30 days after infusion, although more work needs to be done to understand the duration of the antidepressant effect.

Premenstrual dysphoric disorder (PMDD) is a severe form of premenstrual disorder, in which a women experiences depressed mood, mood swings, irritability, anxiety, and changes in sleep and appetite as well as disturbance in functioning at home and/or work prior to menstruation. The Diagnostic and Statistical Manual (DSM-V) provides criteria for diagnosing PMDD. Symptoms associated with PMDD are confirmed by prospective self-ratings that are tracked for at least two complete menstrual cycles. For diagnosis with PMDD a patient must experience at least 5 of the listed criteria for two consecutive menstrual cycles. Approximately 3-8% of women of reproductive age experience premenstrual symptoms severe enough to meet the DMS-V criteria for PMDD. Standard of care treatment for PMDD includes SSRIs, which are considered effective, but require several weeks to provide relief The symptoms of PMDD begin sometime after ovulation, but typically around five days before menses and peak the day before menses or the first day of menses. Symptoms of PMDD respond to treatment with a serotonin reuptake inhibitor (SRI) even when medication is administered for half of the menstrual cycle (2-4) or at symptom-onset. (5, 6) This is atypical since SRIs require weeks to show therapeutic activity for a major depressive episode, panic disorder or generalized anxiety disorder. Given the short onset of therapeutic action of SRIs for PMDD, some hypothesize that SRIs work via a unique mechanism that enhances the production of neuroactive steroids rather reuptake blockade of serotonin. Declining levels of allopregnanolone in the late luteal phase are thought to contribute to PMDD. SSRIs are known to increase allopregnanolone levels and SSRI administration during the late luteal phase is known to alleviate PMDD symptoms.

Postmenopausal depression is a form of major depressive disorder (MDD) with considerable unmet medical need; it is often treatment resistant. Approximately 70% of patients do not respond to standard treatment. Only 30% of patients with postmenopausal depression achieved remission after 8-12 weeks of SSRI therapy. Allopregnanolone levels are inversely correlated with the severity of anxiety and depression symptoms in women across the weight spectrum. Traditional antidepressants may improve depression symptoms by increasing allopregnanolone levels. Allopregnanolone levels are known to increase as major depressive disorder symptoms improve.

Allopregnanolone has been implicated as a treatment for each of the female depressive disorders, postpartum depression, premenstrual dysphoric disorder, and treatment resistant postmenopausal depression. However, allopregnanolone has drug properties that reduce its desirability as a treatment and limit its utility. Allopregnanolone has a short half-life and it cannot be administered orally. While infusion treatment is appropriate for severely depressed patients, many patients would benefit from a pharmaceutical treatment that could initially be administered in an injectable form but that could also be orally administered for longer term therapy. Thus additional treatments may effect improvement through a similar mechanism are desired.

Delirium Tremens (DT) is a severe form of alcohol withdrawal. Onset often occurs 48 to 96 hours after the last drink and it marked by a rapid onset of acute confusion and profound disorientations. DT sufferers may experience tactile, auditory, and visual hallucinations and can experience seizures. ICU hospitalization is recommended. The first line of treatment high dose benzodiazepine; propofol and general anesthesia are administered in refractory cases. Escalating high doses of phenobarbital have also been used clinically. DT can be fatal and has a mortality rate of about 0.5 to 1%. In the US there are approximately 35,000 cases of DT annually with an aggregate cost of treatment of approximately $375 million. There are currently no FDA approved drugs for treating DT and there are no reports of any being developed. Improved treatments for DT that can result in faster recovery, shorten the duration of inpatient hospitalization, and reduce the time of ICU treatment.

SUMMARY

The disclosure provides a method of treating a patient having postpartum depression, premenstrual dysphoric disorder, postmenopausal depression, or delirium tremens comprising administering an effective amount of an injectable neurosteroid formulation to the patient; wherein the injectable neurosteroid formulation is an injectable ganaxolone formulation.

This disclosure includes methods of treating postpartum depression, premenstrual dysphoric disorder, postmenopausal depression, and delirium tremens with two types of injectable neurosteroid formulations. The first such formulation is an injectable formulation containing ganaxolone and sulfobutyl ether β-cyclodextrin in a 1:1 inclusion complex. The second such formulation is an injectable neurosteroid formulation comprising a neurosteroid, preferably ganaxolone, but which may be a neurosteroid selected from allopregnanolone, ganaxolone, alphaxalone, alphadolone, hydroxydione, minaxolone, pregnanolone, tetrahydrocorticosterone, and combinations of the foregoing; a surface stabilizer such as hydroxyl ethyl starch, dextran, and povidone; and a surfactant. This formulation may also contain sucrose to avoid particle agglomeration.

DETAILED DESCRIPTION

Definitions

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced item.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. Thus compositions slightly outside the cited ranges are also encompassed by the scope of the present claims.

An "active agent" is any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers in pure form and mixtures thereof are encompassed. In addition, compounds with carbon-carbon double bonds may occur in Z- and E-forms, with all isomeric forms of the compounds being included in the present invention. In these situations, the single enantiomers, i.e. optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The terms "comprising," "including," and "containing" are non-limiting. Other non-recited elements may be present in embodiments claimed by these transitional phrases. Where "comprising," "containing," or "including" are used as transitional phrases other elements may be included and still form an embodiment within the scope of the claim. The open-ended transitional phrase "comprising" encompasses the intermediate transitional phrase "consisting essentially of" and the close-ended phrase "consisting of"

A "bolus dose" is a relatively large dose of medication administered in a short period, for example within 1 to 30 minutes.

$C_{max}$ is the measured concentration of an active concentration in the plasma at the point of maximum concentration.

The term "inclusion complex" is intended to mean a complex between a ganaxolone molecule and a cyclodextrin molecule. A molecule of ganaxolone may be partially inserted into the hydrophobic cavity of one cyclodextrin molecule. In certain non-limiting embodiments the inclusion complex has one ganaxolone molecule and one sulfobutyl ether-β-cyclodextrin molecule, to give a 1:1 ratio between ganaxolone and sulfobutyl ether-β-cyclodextrin.

Infusion administration is a non-oral administration, typically intravenous though other non-oral routes such as epidural administration are included in some embodiments. Infusion administration occurs over a longer period than a bolus administration, for example over a period of at least 15 minutes, at least 30 minutes, at least 1 hour, at least 2 hours, at least 3 hours, or at least 4 hours.

A "patient" in the context of this disclosure is a human or other mammal in need of medical treatment.

A "therapeutically effective amount" or "effective amount" is that amount of a pharmaceutical agent to achieve a pharmacological effect. The term "therapeutically effective amount" includes, for example, a prophylactically effective amount, that is an amount effective to significantly reduce the probability of occurrence of a disorder in a patient at risk for the disorder. An "effective amount" of neurosteroid is an amount needed to achieve a desired pharmacologic effect or therapeutic improvement without undue adverse side effects. The effective amount of neurosteroid will be selected by those skilled in the art depending on the particular patient and the disorder. It is understood that "an effective amount" or "a therapeutically effective amount" can vary from patient to patient, due to variation in metabolism of neurosteroid, age, weight, general condition of the subject, the condition being treated, the severity of the condition being treated, and the judgment of the prescribing physician. When discussing a method of treating depression, an effective amount includes an amount effective to have a statistically significant and favorable effect on the patient's score on a depression symptoms rating scale. A "Depression symptoms rating scale" refers to any one of a number of standardized questionnaires, clinical instruments, or symptom inventories utilized to measure symptoms and symptom severity in depression. Such rating scales are often used in clinical studies to define treatment outcomes, based on changes from the study's entry point(s) to endpoint(s). Such depression symptoms rating scales include, but are not limited to, the 17 item Hamilton Rating Scale for Depression (HAM-D-17 or $HRSD_{17}$), the 30-Item Inventory of Depressive Symptomatology ($IDS-C_{30}$), The Montgomery-Asperg Depression Rating Scale (MADRS), the Daily Recording of Severity of Problems (DRSP), and the Inventory of Depressive Symptomatology (IDS). Such ratings scales may involve patient self-report or be clinician rated. A 50% or greater reduction in a depression ratings scale score over the course of a clinical trial (starting point to endpoint) is typically considered a favorable response for most depression symptoms rating scales. "Remission" in clinical studies of depression often refers to achieving at, or below, a particular numerical rating score on a depression symptoms rating scale (for instance, less than or equal to 7 on the 17 question $HRSD_{17}$; or less than or equal to 5 on the $QIDS-SR_{16}$; or less than or equal to 10 on the MADRS).

When discussing a method of treating premenstrual dysphoric disorder (PMDD), an effective amount includes an amount effective to have a statistically significant and favorable effect on the patient's score on a depression symptom rating scale, for example the DRSP or IDS. An effective amount of neurosteroid for use in the method of treating PMDD also includes an amount effective to have a statistically significant and favorable effect on the patient's score on the Scale of Premenstrual Tension Syndrome (PMTS).

"Treat" or "treatment" refers to any treatment of a disorder or disease, such as inhibiting the disorder or disease, e.g., arresting the development of the disorder or disease, relieving the disorder or disease, causing regression of the disorder or disease, relieving a condition caused by the disease or disorder, or reducing the symptoms of the disease or disorder. In certain embodiments "treatment" includes prophylactic treatment, that is administering an amount of neurosteroid effective to significantly reduce the probability of occurrence of a disorder or symptoms of a disorder.

Chemical Description

Ganaxolone (CAS Reg. No. 38398-32-2, 3α-hydroxy, 3β-methyl-5α-pregnan-20-one) is a synthetic steroid with anti-convulsant activity useful in treating epilepsy and other central nervous system disorders.

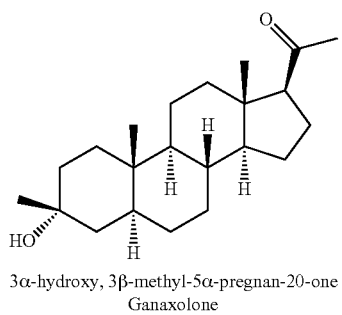

3α-hydroxy, 3β-methyl-5α-pregnan-20-one
Ganaxolone

Ganaxolone has a relatively long half-life-approximately 20 hours in human plasma following oral administration (Nohria, V. and Giller, E., *Neurotherapeutics*, (2007) 4(1): 102-105). Furthermore, ganaxolone has a short $T_{max}$, which means that therapeutic blood levels are reached quickly. Thus initial bolus doses (loading doses) may not be required, which represents an advantage over other anti-depressant or alcohol withdrawal treatments. Ganaxolone is useful for treating seizures in adult and pediatric epileptic patients.

Allopregnanolone (CAS Reg. No. 516-54-1, 3 α, 5α-tetrahydroprogesterone) is an endogenous progesterone derivative with anti-convulsant activity.

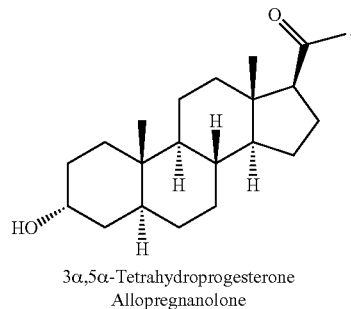

3α,5α-Tetrahydroprogesterone
Allopregnanolone

Allopregnanolone has a relatively short half-life, about 45 minutes in human plasma.

Alphaxalone, also known as alfaxalone, (CAS Reg. No. 23930-19-0, 3α-hydroxy-5α-pregnan-11,20-dione) is a neurosteroid with an anesthetic activity. An injectable nanoparticle neurosteroid dosage form containing alphaxalone alone or in combination with either ganaxolone or allopregnanolone is within the scope of this disclosure.

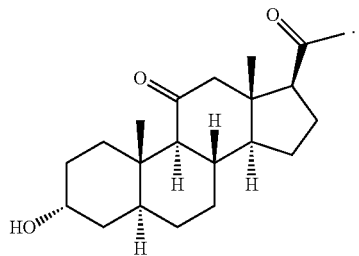

3α-hydroxy, 5α-pregnan-11,20-dione
Alphaxalone

Alphadolone, also known as alfadolone, (CAS Reg. No. 14107-37-0, 3α, 21-dihydroxy-5α-pregnan-11,20-dione) is a neurosteroid with anesthetic properties.

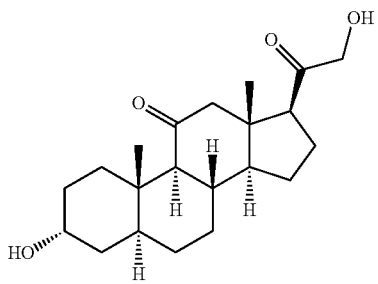

3α, 21-dihydroxy-5α-pregnane-11,20-dione
Alphadolone

Additional neurosteroids that may be used in the injectable nanoparticle neurosteroid formulation of this disclosure include formulations include hydroxydione (CAS Reg. No. 303-01-5, (5β)-21-hydroxypregnane-3,20-dione), minaxolone (CAS Reg. No. 62571-87-3, 2β,3α,5α,11α)-11-(dimethylamino)-2-ethoxy-3-hydroxypregnan-20-one), pregnanolone (CAS Reg. No. 128-20-1, (3α,5β)-d-hydroxypreganan-20-one), renanolone (CAS Reg. No. 565-99-1, 3α-hydroxy-5β-pregnan-11,20-dione), or tetrahydrocorticosterone (CAS Reg. No. 68-42-8, 3α,5α-pregnan-20-dione).

This disclosure includes methods of treating postpartum depression, premenstrual dysphoric disorder, postmenopausal depression, and delirium tremens with two types of injectable neurosteroid formulations. The first such formulation is an injectable formulation containing ganaxolone and sulfobutyl ether β-cyclodextrin in a 1:1 inclusion complex. The second such formulation is an injectable neurosteroid formulation comprising a neurosteroid selected from allopregnanolone, ganaxolone, alphaxalone, alphadolone, hydroxydione, minaxolone, pregnanolone, tetrahydrocorticosterone, and combinations of the foregoing; a surface stabilizer, preferably selected from hydroxyl ethyl starch, dextran, and povidone; and a surfactant.

Injectable Substituted Beta-Cyclodextrin-Ganaxolone Formulations

U.S. Pat. Nos. 5,134,127 and 5,376,645 each to Stella et al. disclose sulfoalkyl ether cyclodextrin derivatives and their use as solubilizing agents for water-insoluble drugs for oral, intranasal or parenteral administration including intravenous and intramuscular administration. Stella et al. disclose an inclusion complex of the water-insoluble drug and the sulfoalkyl ether cyclodextrin derivative, and pharmaceutical compositions containing these inclusion complexes. Examples of sulfoalkyl ether cyclodextrin derivatives disclosed include mono-sulfobutyl ethers of β-cyclodextrin and monosulfopropyl ethers of β-cyclodextrin. CAPTISOL, marketed by Ligand Pharmaceuticals is a sulfobutyl ether β-cyclodextrin with an average 6-7 sulfobutyl ether groups per cyclodextrin molecule. CAPTISOL is sold as an amorphous material and has an average molecular weight of 2163 g/ mole based on 6.5 substitutions per molecule.

The disclosure provides injectable substituted β-cyclodextrin ganaxolone formulations, including formulations containing CAPTISOL-ganaxolone inclusion complexes. Injectable substituted β-cyclodextrin ganaxolone formulations disclosed herein include formulations suitable for intramuscular, intravenous, intraarterial, intraspinal, and intrathecal injection. Injectable formulations include parenteral formulations suitable for intravenous infusion. Suitable injectable substituted β-cyclodextrin -ganaxolone formulations for use in the methods of this disclosure include formulations disclosed in U.S. Ser. No. 15/276,203 and U.S. Ser. No. 15/018,258 both of which are hereby incorporated by reference in their entirety.

The disclosure provides methods of using injectable substituted β-cyclodextrin ganaxolone formulations containing an inclusion complex of a substituted-β-cyclodextrin, such as CAPTISOL, and ganaxolone, and a pharmaceutically acceptable carrier. In certain embodiments the substituted β-cyclodextrin ganaxolone formulation of the disclosure will be in the form of an aqueous parenteral or injectable formulation.

Ganaxolone is very poorly soluble in water (<0.001 mg/mL) and thus is difficult to formulate as an aqueous injectable. The inventors have found that the water-solubility of ganaxolone may be sufficiently increased to allow it to be formulated as an aqueous injectable by complexing ganaxolone with a substituted β-cyclodextrin, such as CAPTISOL. In effect, the substituted β-cyclodextrin inhibits precipitation of the ganaxolone at the injection site, providing reduced irritation and permitting injection without unacceptable injection-site irritation.

The disclosure provides methods of using injectable substituted β-cyclodextrin ganaxolone formulations containing ganaxolone at a concentration of 0.25 mg/mL, 0.5 mg/mL, 1.0 mg/mL, 1.5 mg/mL, 2.0 mg/mL, 2.5 mg/mL, 3.0 mg/mL, 3.5 mg/mL, 4.0 mg/mL, 4.5 mg/mL. 5.0 mg/mL, 5.5 mg/mL, 6.0 mg/mL, 6.5 mg/mL, 7.0 mg/mL, 7.5 mg/mL, 8.0 mg/mL, 8.5 mg/ mL, 9.0 mg/mL, 10 mg/mL, 11 mg/ mL, 12 mg/mL, 13 mg/mL, or about 15 mg/mL. All ranges including any two of the foregoing concentrations of substituted β-cyclodextrin as endpoints are also included in the disclosure. For example, the disclosure includes methods using substituted β-cyclodextrin ganaxolone formulations containing from about 0.5mg/mL, to about 15 mg/mL, about 1.0 mg/mL to about 10 mg/mL, about 2.0 mg/mL to about 8.0 mg/mL, or about 4.0 mg/mL to about 8.0 mg/mg ganaxolone. An embodiment comprising a method of using an aqueous injectable ganaxolone/sulfobutyl ether β-cyclodextrm formulation (e.g. in an inclusion complex) and containing from about 2.0 mg/mL, to about 8.0 mg/mL ganaxolone is included in this disclosure.

The substituted β-cyclodextrin used in the methods of this disclosure will be in a weight: weight ratio to ganaxolone of about 10:1 to 100: 1, or about 40:1 to about 80:1, or about 52:1 to about 80:1, or about 52:1 to about 85:1, or about 55:1 to about 70:1, or about 55:1 to about 65:1 or about 55:1. The ratio of substituted β-cyclodextrin to ganaxolone needed to inhibit or prevent precipitation of ganaxolone in the formulation or upon injection depends on the particular type of substituted-β-cyclodextrin used. When CAPTISOL is used a CAPTISOL:ganaxolone ratio of about 52:1 to about 85:1, or about 55:1 to about 70:1, or about 55:1 to about 65:1 or about 55:1 is required. The substituted β-cyclodextrin may be present in an amount greater than that needed to complex the ganaxolone to aid in ganaxolone solubilization.

In methods disclosed herein the ganaxolone and sulfobutyl ether-β-cyclodextrin may be in an inclusion complex, and the inclusion complex may be a 1:1 ganaxolone: sulfobutyl ether-β-cyclodextrin complex.

In certain embodiments the ganaxolone and sulfobutyl ether-β-cyclodextrin inclusion complex provides at least 2.0 mg/mL ganaxolone (or at least 0.1 mg/mL, or at least 1.0 mg/mL, or at least 11.5 mg/ mL), when the amount of ganaxolone provided by the complex is measured at a sulfobutyl ether-β-cyclodextrin concentration of 30% w/v in water. In certain embodiments the ganaxolone concentration is about 0.1 mg/ml to about 15 mg/ml, or about 1 mg/ml to about 10 mg/ml, or about 1 mg/ml to about 5 mg/ml.

In certain embodiments ganaxolone will be present in the aqueous injectable formulation in an amount of from about 0.1 to about 5% by weight, or from about 0.2 to about 2.5%, or from about 0.5 to about 1.5% by weight based on the total injectable formulation weight.

The disclosure also provides methods in which the injectable substituted β-cyclodextrin ganaxolone formulations containing substituted β-cyclodextrin at a concentration of 5mg/mL, 10 mg/mL, 50 mg/mL, 100 mg/mL, 150 mg/mL, 200 mg/mg/mL, 250 mg/mL, 300 mg/mL, 350 mg/ mL, 400 mg/mL, 450 mg/mL, 500 mg/mL, 550 mg/mL, 600 mg/mL, 650 mg/mL, or 700 mg/mL so long as the ratio of substituted β-cyclodextrin to ganaxolone is about 52:1 or greater. All ranges including any two of the foregoing concentrations of substituted β-cyclodextrin as endpoints are also included in the disclosure. For example, the disclosure includes substituted β-cyclodextrin ganaxolone formulations containing from about 5 mg/mL to about 500 mg/mL, or about 50 mg/mL to about 500 mg/mL, or about 100 mg/mL to about 400 mg/mL substituted β-cyclodextrin. The disclosure includes an embodiment in which the substituted β-cyclodextrin ganaxolone formulations contain from about 25 mg/mL to about 400 mg/mL sulfobutyl ether-β-cyclodextrin.

Ganaxolone will form a complex with substituted-β-cyclodextrin which complex may be dissolved in water to form an injectable formulation. However, physical mixtures of ganaxolone and substituted-β-cyclodextrin are within the scope of the disclosure.

The disclosure includes methods in which the ganaxolone-sulfobutyl ether-β-cyclodextrin formulation additionally comprises a buffer, such as an acetate, citrate, tartrate, phosphate, or triethanolamine (TRIS) buffer an acid or base buffer to adjust pH to desired levels. In some embodiments the desired pH is 2.5-11.0, 3.5-9.0, or 5.0-8.0, or 6.0-8.0, or 6.8-7.6, or 6.80-7.10, or about 7.4. Examples of acid buffers useful in the substituted β-cyclodextrin-ganaxolone formulation include oxalic acid, maleic acid, fumaric acid, lactic acid, malic acid, tartaric acid, citric acid, benzoic acid, acetic acid, methanesulfonic acid, histidine, succinic acid, toluenesulfonic acid, benzenesulfonic acid, ethanesulfonic acid and the like. Acid salts of the above acids may be employed as well. Examples of base buffers useful in the formulation include carbonic acid and bicarbonate systems such as sodium carbonate and sodium bicarbonate, and phosphate buffer systems, such as sodium monohydrogen phosphate and sodium dihydrogen phosphate. In certain embodiments the buffer is a phosphate buffer. In certain embodiments the buffer is phosphate buffered saline. In certain embodiments the buffer is a mixture of monobasic and dibasic phosphate buffers, such as potassium phosphate mono or dibasic phosphate buffers. The concentration of each component of a phosphate buffer system will be from about 5 mM to about 20 mM, about 10 mM to about 200 mM, or from about 20 mM to about 150 mM, or from about 50 mM to about 100 mM.

The disclosure includes embodiments in which the of the ganaxolone -sulfobutyl ether-β-cyclodextrin formulation is about 6.9, 7.0, 7.1, 7.2, 7.3, or 7.4.

The disclosure includes methods in which the formulation contains electrolytes, such as sodium or potassium and in which the formulation is from about 0.5% to about 1.5% sodium chloride (saline).

The disclosure includes methods in which the formulation contains tonicity adjusting agents so that it is isotonic with human plasma. Examples of tonicity adjusting agents useful in the formulation include, but are not limited to, dextrose, mannitol, sodium chloride, or glycerin. In certain embodiments the tonicity agent is 0.9% sodium chloride.

The substituted cyclodextrin-ganaxolone injectable formulation used in the methods of this disclosure may contain a non-aqueous carrier. Non-aqueous carriers include any pharmaceutically acceptable excipient compatible with ganaxolone and capable of providing the desired pharmacological release profile for the dosage form. Carrier materials include, for example, suspending agents, surfactants, solubilizers, stabilizers, lubricants, wetting agents, diluents, and the like. "Pharmaceutically compatible carrier materials" may comprise, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The substituted β-cyclodextrin-ganaxolone injectable formulation may also contain a non-aqueous diluent such as ethanol, one or more polyol (e.g glycerol, propylene glycol), an oil carrier, or any combination of the foregoing.

The substituted β-cyclodextrin-ganaxolone injectable formulation of the may additionally comprise a preservative. The preservative may be used to inhibit bacterial growth. Preservatives suitable for parenteral formulations include benzyl alcohol, chlorbutanol, 2-ethoxyethanol, parabens (methyl, ethyl, propyl, butyl, and combinations), benzoic acid, sorbic acid, chlorhexidene, phenol, 3-cresol, thimerosal, and phenylmercurate salts.

The substituted β-cyclodextrin-ganaxolone injectable formulation may optionally include a coating or surfactant to insure desirable solubilization and fluidity of ganaxolone in the substituted β-cyclodextrin, such as CAPTISOL.

Surfactants include compounds such as lecithin (phosphatides); sorbitan trioleate and other sorbitan esters; polyoxyethylene sorbitan fatty acid esters (e.g., the commercially available TWEENS such as polyoxyethylene sorbitan monolaurate (TWEEN 20, also known as Polysorbate 20, CAS Reg. No. 9005-64-5) and polyoxyethylene sorbitan monooleate (TWEEN 80, ICI Speciality Chemicals, also known as Polysorbate 80 (CAS Reg. No. 9005-65-6)); poloxamers (e.g., poloxamer 188 (PLURONIC F68) and poloxamer 338 (PLURONIC F108), which are block copolymers of ethylene oxide and propylene oxide, and poloxamer 407, which is a triblock copolymer of propylene glycol and two blocks of polyethylene glycol); sodium cholesterol sulfate or other cholesterol salts; and bile salts, such as sodium deoxycholate, sodium cholate, sodium glycholate, salts of deoxycholic acid, salts of glycholic acid, salts of chenodeoxycholic acid, and salts of lithocholic acid.

The substituted β-cyclodextrin-ganaxolone injectable formulation may comprise a substituted β-cyclodextrin-ganaxolone injectable formulation containing (1) ganaxolone, from 2 to about 8 mg/mL, (2) CAPTISOL, from about 100 to about 400 mg/mL, (3) phosphate buffer to adjust to from about 7.0 to about 7.5, and (4) water. The β-cyclodextrin-ganaxolone injectable formulation may be aseptically filtered, for example, through a 0.2 μm membrane filter. The β-cyclodextrin-ganaxolone injectable formulation may be autoclaved or lyophilized for storage and reconstitution.

The disclosure includes any β-cyclodextrin-ganaxolone injectable formulation as described in this disclosure that also meet the following requirements. Any of the following requirements can he combined so long as a stable formulation results. In any of the disclosed injectable β-cyclodextrin-ganaxolone injectable formulations, the ganaxolone and the sulfobutyl ether-β-cyclodextrin are in the form of an inclusion complex.

(a) The β-cyclodextrin-ganaxolone injectable formulation includes a surfactant and the surfactant is a sorbitan ester, sodium deoxycholoate, a polyoxyethylene sorbitan fatty acid ester, a poloxamer, a cholesterol salt, or a bile salt.

(b) The β-cyclodextrin-ganaxolone injectable formulation is about 0.05 to about 15 weight percent surfactants.

(c) The β-cyclodextrin-ganaxolone injectable formulation includes a surfactant wherein the surfactant is polysorbate 80.

(d) The β-cyclodextrin-ganaxolone injectable formulation includes a buffer.

(e) The β-cyclodextrin-ganaxolone injectable formulation includes a buffer having a pH of about 6.8 to about 7.6.

(f) The β-cyclodextrin-ganaxolone injectable formulation includes a phosphate buffer. In certain embodiments the phosphate buffer is phosphate buffered saline. The buffer is a combination of a monobasic phosphate buffer and a dibasic phosphate buffer, wherein the concentration of each phosphate buffer is 2 mM to 50 mM. In certain embodiments the phosphate buffer is a combination of a monobasic phosphate buffer and a dibasic phosphate buffer, wherein the concentration of each phosphate buffer is 2 mM to 50 mM.

(g) The β-cyclodextrin-ganaxolone injectable formulation includes a concentration of ganaxolone that is 2 mg/ml to 8 mg/ml; the w/w ratio of sulfobutyl ether-β-cyclodextrin to ganaxolone is within the range from about 52:1 to about 90:1, or about 52:1 to about 80:1, or about 55:1 to about 70:1; or at least 55:1; the formulation contains a buffer and has a pH of 6.7 to 7.3; and the formulation contains from 0.5 to 15 weight percent surfactant, or about 1 to about 10 weight percent surfactant; or about 10 weight percent surfactant.

(h) The sulfobutyl ether β-cyclodextrin-ganaxolone injectable formulation includes a concentration of ganaxolone that is from 1 mg/ml to 5 mg/ml; the weight percent of sulfobutyl ether-β-cyclodextrin 20% to 40%; or 25% to 35%, or about 30% sulfobutyl ether β-cyclodextrin and the formulation contains from 5% to 20%; 5% to 15%; or about 10% (weight percent) of at least one of the following: a surfactant, ethanol, glycerin or propylene glycol. In certain embodiments this formulation may contain a surfactant chosen from lecithin (phosphatides); sorbitan trioleate and other sorbitan esters; polyoxyethylene sorbitan fatty acid esters (e.g., the commercially available TWEENS such as polyoxyethylene sorbitan monolaurate and polyoxyethylene sorbitan monooleate; poloxamers (e.g., poloxamer 188 (PLURONIC F68) and poloxamer 338 (PLURONIC F108), which are block copolymers of ethylene oxide and propylene oxide, and poloxamer 407, which is a triblock copolymer of propylene glycol and two blocks of polyethylene glycol); sodium cholesterol sulfate or other cholesterol salts; and bile salts (i) The β-cyclodextrin-ganaxolone injectable formulation includes a preservative. In certain embodiments the preservative is benzyl alcohol, chlorbutanol, 2-ethoxyethanol, parabens (including methyl, ethyl, propyl, butyl, and combinations), benzoic acid, sorbic acid, chlorhexidene, phenol 3-cresol, thimerosal, or a phenylmercurate salt.

(j) The sulfobutyl ether-β-cyclodextrin are in the form of an inclusion complex, wherein the inclusion complex provides at least 2.0 mg/mL ganaxolone, when the amount of ganaxolone provided by the complex is measured at a sulfobutyl ether-β-cyclodextrin concentration of about 30% w/v in water.

(k) The β-cyclodextrin-ganaxolone injectable formulation includes ethanol, e.g. 1 to 20 percent (volume/volume). 5 to 15 percent (v/v), or about 10 percent ethanol (v/v).

(l) The β-cyclodextrin-ganaxolone injectable formulation includes a wetting agent. In certain embodiments the solubilizing agent is glycerin or propylene glycol, e.g. 1 to 20 percent (volume/volume), 5 to 15 percent (v/v), or about 10 percent (v/v).

Injectable Neurosteroid Nanoparticle Formulations

This disclosure includes methods of using injectable nanoparticle formulations, including formulations suitable for intravenous administration. The neurosteroid nanoparticles contain a neurosteroid, a surface stabilizer, (such as a polymeric surface stabilizer, for example hydroxyl ethyl starch, dextran, lecithin, Poloxamer 188, Polysorbate 80, or povidone) and a surfactant. In certain embodiments the neurosteroid, may be ganaxolone or allopregnanolone.

The injectable neurosteroid nanoparticle formulations, including formulations containing nanoparticles comprising a neurosteroid, a surface stabilizer, such as either hydroxyethyl starch or dextran, and a surfactant. In certain embodiments the nanoparticles comprise ganaxolone or allopregnanolone, hydroxyethyl starch, and a surfactant. Injectable neurosteroid nanoparticle formulations disclosed herein include formulations suitable for intramuscular, intravenous, intraarterial, intraspinal, subcutaneous, and intrathecal injection. Injectable formulations include parenteral formulations suitable for intravenous infusion.

In certain embodiment the surface stabilizer is a blood replacer, such as a blood volume expander. In certain embodiments the surface stabilizer is either hydroxyethyl starch, dextran, or povidone. Hydroxyethyl starch is used as a blood volume expander in patients suffering from severe blood loss. Grades of hydroxyethyl starch suitable for use in the neurosteroid nanoparticles include 130/0.4 (CAS Reg. No. 9005-27-0). In certain embodiments the surface stabilizer is dextran. Dextran is a single chain branched glucan having chains of varying lengths. Like hydroxyethyl starch, dextran is also used as a blood volume expander. Dextrans are classified according to MW. Dextrans having molecular weights from 40 kD to 75 kD have been used as blood volume expanders. Suitable dextrans for intravenous use include Dextran 40, Dextran 60, Dextran 70, and Dextran 75. In certain embodiments the surface stabilizer is a dextran having a molecular weight from about 40 kD to about 75 kD. In certain embodiments the surface stabilizer is Dextran 70. Povidone, also known as polyvinylpyrrolidone, is another approved plasma expander. Low molecular weight polyvinylpyrrolidone (C12-C17) is another approved excipient that may be used in intravenous drug products. Other excipients useful as surface stabilizers for the injectable neurosteroid nanoparticle formulation include human serum albumin, hydrolyzed gelatin, polyoxyethylene castor oil, and polyoxyethylene hydrogenated castor oil. Suitable injectable ganaxolone nanoparticle formulations for use in the methods of this disclosure include formulations disclosed in U.S. Ser. No. 15/294,135 which is hereby incorporated by reference in its entirety.

The weight to weight ratio of neurosteroid to surface stabilizer is about 10:1 to 0.5: 1, or about 5:1 to about 0.5:1, or about 4:1 to about 1:1, or about 3.5:1 to about 3:1, or about 3.3:1.

The injectable neurosteroid nanoparticle injectable formulation includes a surfactant. Surfactants suitable for use in the neurosteroid nanoparticle formulations include compounds such as lecithin (phosphatides), sorbitan trioleate and other sorbitan esters, polyoxyethylene sorbitan fatty acid esters (e.g., the commercially available TWEENS such as polyoxyethylene sorbitan monolaurate (TWEEN 20) and polyoxyethylene sorbitan monooleate (TWEEN 80) (ICI Speciality Chemicals)); poloxamers (e.g., poloxamer 188 PLURONIC F68 and poloxamer 338 (PLURONIC F108), which are block copolymers of ethylene oxide and propylene oxide), lecithin, sodium cholesterol sulfate or other cholesterol salts, and bile salts, such as sodium deoxycholate. Additional bile salts that may be used as surfactants include sodium cholate, sodium glycholate, salts of deoxycholic acid, salts of glycholic acid, salts of chenodeoxycholic acid, and salts of lithocholic acid.

The injectable neurosteroid nanoparticle formulations may also include an acid or base buffer to adjust pH to desired levels. In some embodiments the desired pH is 2.5-11.0, 3.5-9.0, or 5.0-8.0, or 6.0-8.0, or 7.0-7.6, or about 7.4. Examples of acid buffers useful in the injectable neurosteroid nanoparticle formulation include oxalic acid, maleic acid, fumaric acid, lactic acid, malic acid, tartaric acid, citric acid, benzoic acid, acetic acid, methanesulfonic acid, histidine, succinic acid, toluenesulfonic acid, benzenesulfonic acid, ethanesulfonic acid and the like. Acid salts of the above acids may be employed as well. Examples of base buffers useful in the formulation include carbonic acid and bicarbonate systems such as sodium carbonate and sodium bicarbonate, and phosphate buffer systems, such as sodium monohydrogen phosphate and sodium dihydrogen phosphate. In certain embodiments the buffer is a phosphate buffer. In certain embodiments the buffer is phosphate buffered saline. The concentration of each component of a phosphate buffer system will be from about 10 mM to about 200 mM, or from about 20 mM to about 150 mM, or from about 50 mM to about 100 mM.

The disclosure includes embodiments in which the pH of the neurosteroid nanoparticle formulation is about 7.4.

The formulation may contain electrolytes, such as sodium or potassium. The disclosure includes embodiments in which the formulation is from about 0.5% to about 1.5% sodium chloride (saline).

The formulation may contain tonicity adjusting agents so that it is isotonic with human plasma. Examples of tonicity adjusting agents useful in the formulation include, but are not limited to, dextrose, mannitol, sodium chloride, or glycerin. In certain embodiments the tonicity agent is 0.9% sodium chloride.

The injectable neurosteroid nanoparticle formulation may include an antifoaming agent. Suitable antifoaming agents include dimethicone, myristic acid, palmitic acid, and simethicone.

The injectable neurosteroid nanoparticle formulation used in the disclosed methods can also contain a non-aqueous diluent such as ethanol, one or more polyol (e.g. glycerol, propylene glycol), an oil carrier, or any combination of the foregoing.

The injectable neurosteroid nanoparticle formulation used in the disclosed methods can additionally comprise a preservative. The preservative may be used to inhibit bacterial growth or prevent deterioration of the active agent. Preservatives suitable for parenteral formulations include ascorbic acid, acetylcysteine, benzalkonium chloride, benzethonium chloride, benzoic acid, benzyl alcohol, chlorbutanol, chlorhexidene, m-cresol, 2-ethoxyethanol, human serum albumin, monothioglycerol, parabens (methyl, ethyl, propyl, butyl, and combinations), phenol, phenylmercurate salts (acetate, borate nitrate), sorbic acid, sulfurous acid salts (bisulfite and metabisulfite), and thimerosal. In certain embodiments the preservative is an antioxidants such ascorbic acid, glutathione, or an amino acid. Amino acids useful as antioxidants include methionine, cysteine, and L-arginine.

The injectable neurosteroid nanoparticle formulations may contain any additional pharmaceutically acceptable excipient compatible with the neurosteroid and capable of providing the desired pharmacological release profile for the dosage form. Additional excipients include, for example, suspending agents, solubilizers, stabilizers, lubricants, wetting agents, and the like. Pharmaceutically acceptable excipients may comprise, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

Neurosteroid nanoparticles have a volume weighted median diameter (D50) of from about 10 to about 2000 nm, from about 10 nm to about 350 nm, or having a D50 of from about 50 nm to about 300 nm, or having a D50 of from about 100 nm to about 250 nm, or having a D50 of about 150 nm to about 220 nm, or having a D50 of less than 350 nm, less than 300 nm, less than 250 nm, or less than 200 nm.

In one aspect the neurosteroid nanoparticles have at least one of the following properties: (a) greater than 90% of the neurosteroid by weight is in the form of submicron particle having an effective size of about 50 nm to about 250 nm; (b) at least about 20% of the neurosteroid by weight is in the form of an amorphous powder; (c) at least about 50% of the neurosteroid by weight is in the form of a crystalline powder of a single polymorph; (d) at least about 50% of the neurosteroid is in the form of a semi-crystalline powder; (e) the neurosteroid is in the form of particles wherein at least about 50%, or at least 60%, or at least 70%, or at least 80%, or at least 90% of the particles by weight have an effective size less than 300 nm; (f) the neurosteroid is in the form of particles wherein at least about 50% of the particles by weight have and effective size less than 250 nm; (g) the neurosteroid is in the form of particles having a D50 of about 50 nm to about 200 nm, wherein the particle size distribution is described by a three-slice model in which a certain percentage has an effective particle size by weight between about 10 nm and about 100 nm, a certain percentage has an effective particle size by weight between about 100 nm and about 200 nm, and a certain percentage has an effective particle size by weight above 200 nm, and further wherein the three-slice model is identified as x %/y %/z %, respectively (e.g., 40%/30%/30%); (p) the neurosteroid has a three-slice distribution selected from the group 40%/30%/30%, 50%/30%/20%, 60%/30%/10%, 40%/40%/20%, 50%/40%/10%, 70%/20%/10%, 50%/45%/5%, 70%/25%/5%, 60%/35%/5%, 80%/15%/5%, 70%/30%/0%, 60%/40%/0%, 90%/10%/0%, and 100%/0%/0%; (h) the neurosteroid is in the form of particles, wherein standard deviation of the particle size distribution divided by the volume-weighted mean diameter is less than about 30%, less than about 25%, less than about 20%, less than about 15%, or less than about 10%. In alternative embodiments, the neurosteroid in the composition has at least two of the aforementioned properties; at least about three of the aforementioned properties; at least about four of the aforementioned properties; or at least five of the aforementioned properties.

The neurosteroid nanoparticles may be prepared by grinding. Grinding can take place in any suitable grinding mill. Suitable mills include an air jet mill, a roller mill, a ball mill, an attritor mill, a vibratory mill, a planetary mill, a sand mill and a bead mill. A high energy media mill is preferred when small particles are desired. The mill can contain a rotating shaft.

The preferred proportions of the grinding media, neurosteroid, the optional liquid dispersion medium, and dispersing, wetting or other particle stabilizing agents present in the grinding vessel can vary within wide limits and depends, for example, the size and density of the grinding media, the type of mill selected, the time of milling, etc. The process can be carried out in a continuous, batch or semi-batch mode. In high energy media mills, it can be desirable to fill 80-95% of the volume of the grinding chamber with grinding media. On the other hand, in roller mills, it frequently is desirable to leave the grinding vessel up to half filled with air, the remaining volume comprising the grinding media and the liquid dispersion media, if present. This permits a cascading effect within the vessel on the rollers which permits efficient grinding. However, when foaming is a problem during wet grinding, the vessel can be completely filled with the liquid dispersion medium or an anti-foaming agent may be added to the liquid dispersion.

The attrition time can vary widely and depends primarily upon the drug, mechanical means and the residence conditions selected, the initial and desired final particle size, and so forth.

After attrition is completed, the grinding media is separated from the milled neurosteroid particulate product (in either a dry or liquid dispersion form) using conventional separation techniques, such as by filtration, sieving through a mesh screen, and the like.

In one aspect, the grinding media comprises beads having a size ranging from 0.05-4 mm, preferably 0.1-0.4 mm. For example, high energy milling of neurosteroid with yttrium stabilized zirconium oxide 0.4 mm beads for a milling residence time of 25 minutes to 1.5 hours in recirculation mode at 2500 RPM. In another aspect the grinding media may be a polymeric milling media, which has the advantages of reduced heaving metal contamination and is compatible with steam-in-place or autoclave sterilization/sanitation of the milling equipment and media. In another example, high energy milling of neurosteroid with 0.1 mm zirconium oxide balls for a milling residence time of 2 hours in batch mode. Additionally, the milling temperatures, for certain of the disclosed embodiments, should not exceed 50° C. as the viscosity of the suspension may change. However, temperature limits are formulation specific. High temperature can exceed the cloud point of certain polymeric stabilizers and lead to agglomeration or viscosity increase. But, milling above 50° C. may be desirable for some formulations. The milling concentration is from about 1% to about 40% neurosteroid by weight. In one embodiment, the concentration is 25% neurosteroid by weight. In one embodiment, the milling media contains at least one agent to adjust viscosity so that the desired particles are suspended evenly, and a wetting and/or dispersing agent to coat the initial neurosteroid suspension so a uniform feed rate may be applied in continuous milling mode. In another embodiment, batch milling mode is utilized with a milling media containing at least one agent to adjust viscosity and/or provide a wetting effect so that the neurosteroid is well dispersed amongst the grinding media.

The disclosure provides methods of using injectable neurosteroid nanoparticle formulationscontaining the neurosteroid at a concentration of about 0.25 mg/mL, about 0.5 mg/mL, about 1.0 mg/mL, about 1.5 mg/mL, about 2.0 mg/mL, about 2.5 mg/mL, about 3.0 mg/mL, about 3.5 mg/mL, about 4.0 mg/mL, about 4.5 mg/mL, about 5.0 mg/mL, about 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, about 10 mg/mL, about 11 mg/mL, about 12 mg/mL, about 13 mg/mL, or about 15 mg/mL, about 30 mg/mL, about 40 mg/mL, about 50 mg, mL, about 75 mg/ mL, or about 100 mg/mL. All ranges including any two of the foregoing concentrations of neurosteroid as endpoints are also included in the disclosure. For example, the disclosure includes neurosteroid nanoparticle formulations containing from about 0.5mg/mL to about 15 mg/mL, about 1.0 mg/mL to about 10 mg/mL, about 2.0 mg/mL to about 8.0 mg/mL, or about 4.0 mg/mL to about 8.0 mg/mL, about 1.0 mg/mL to about 100 mg/mL, about 10 mg/mL to about 100 mg/mL, or about 30 mg/mL to about 50 mg/ mL neurosteroid.

Methods of Treatment

Methods of treatment include treating a patient suffering from postpartum depression, premenstrual dysphoric disorder, menopausal depression, or delirium tremens by administering the injectable neurosteroid formulation as a single dose (bolus dose), a series of bolus doses, a continuous infusion, or a combination of one or more bolus doses and a continuous infusion. In certain embodiments the injectable neurosteroid formulation of the disclosure is administered intramuscularly or intravenously.

Administration of the injectable neurosteroid formulation may be followed by oral administration of the neurosteroid.

The single bolus dose of any formulation of this disclosure may be an injection and may be administered intramuscularly or intravenously. The dose of the single injection may be from about 1 mg/kg to about 20 mg/kg, from about 2 mg/kg to about 15 mg/kg, from about 2 mg/kg to about 10 mg/kg, or about 2 mg/kg to about 8 mg/kg. Methods of treatment also include administering multiple injections of the disclosed formulations over a period of 1 to 10 days. The injections may be given at intervals of 1 to 24 hours. Dosing schedules in which the injectable formulation is injected every 1 hour, 2 hours, 4 hours, 6 hours, 8 hours, 12 hours, or 24 hours are included herein. Dosing schedules in which the injectable formulation is injected for 1, 2, 3, 4, 5, 6, 7, 8, 9, or 10 days are included herein.

Methods of treatment include treating a patient suffering from postpartum depression, premenstrual dysphoric disorder, menopausal depression, or delirium tremens by administering one or more bolus doses over a period of 10 days as described in the preceding paragraph of an injectable formulation of this disclosure followed by an intravenous infusion of the injectable formulation. In certain embodiments the bolus dose is administered over a period of about 1 to about 60, 1 to about 30. about 1 to about 15, about 1 to about 10, or about 1 to about 5, or about 5 minutes followed by commencement of the intravenous infusion within 1, 2, 3, 4, or 5 hours.

In some embodiments, an injectable formulation of this disclosure is administered as an intravenous infusion dose, either without or without a previous bolus dose for 1, 2, 3, 4. 5, 6, 7, 8, 9, or 10 consecutive days. The infusion. dose may be administered at a rate of 1, 2, 3, 4, 5, 6, 7, 8, 9, or 10 mg/kg/hr or in a range of about 1 mg/kg/hr to about 10 mg/kg/hr or 2 mg/kg/hr to about 8 mg/kg/hrs.

In some embodiments the infusion dose (whether administered with or without the bolus dose) is followed by a first step down dosage, and optionally a second step down dosage, an optionally a third step down infusion dosage. In some embodiments, the first step dose is 95%, 90%, 85%, 80%, 75%, 70%, 65%, 60%, 55%, 50%, 45%, 40%, 35%, 30%, 25%, 20%, 15%, 10%, or 5% of the infusion dose. In some embodiments, the first step dose is between 95-50%, 75-50%, 85-50%, 90-50%, 80-50%, or 75-100% of the infusion dose. In an embodiment, the first step dose is 75% of the infusion dose. In some embodiments, the second step dose is 95%, 90%, 85%, 80%, 75%, 70%, 65%, 60%. 55%, 50%, 45%, 40%, 35%, 30%, 25%, 20%, 15%, 10%, or 5% of the first step down dose. In some embodiments, the second step dose is between 95-30%, 75-30%, 85-30%, 60-30%, 70-30%, 50-30%, or 50-40% of the first step down dose. In an embodiment, the second step dose is 50% of the infusion dose. In some embodiments, the third step dose is 95%, 90%, 85%, 80%, 75%, 70%, 65%, 60%, 55%, 50%, 45%, 40%, 35%, 30%, 25%, 20%, 15%, 10%, or 5% of the second infusion dose. In some embodiments, the third step dose is between 50-5%, 40-5%, 30-5%, 25-5%, 25-10%, 25-20%, or 25-40% of the second step down dose. In an embodiment, the third step down dose is 25% of the infusion dose.

The disclosure includes methods of treating a patient suffering from postpartum depression, premenstrual dysphoric disorder, menopausal depression, or delirium tremens administering an effective amount an injectable neurosteroid formulation of this disclosure to a patient wherein the amount of neurosteroid, e.g. ganaxolone, administered is from about 0.1 mg/kg to about 200 mg/kg.

The disclosure includes embodiments in which the injectable neurosteroid formulation is a ganaxolone formulation and is administered as a single bolus dose of the ganaxolone formulation to the patient. In certain embodiments the single bolus dose provides a sufficient amount of ganaxolone to provide a plasma $C_{max}$ of ganaxolone of about 20 ng/mL to about 1000 ng/mL in the patient. The disclosure includes a method of treating postpartum depression in which the bolus dose provides a plasma $C_{max}$ of ganaxolone of 60 ng/ml.

The disclosure includes embodiments in which the injectable neurosteroid formulation is a ganaxolone formulation and is administered as a bolus dose and the bolus dose provides a sufficient amount of ganaxolone to provide a plasma $C_{max}$ of ganaxolone of about 20 ng/mL to about 900 ng/mL in the patient.

The disclosure includes embodiments in which the injectable neurosteroid formulation is a ganaxolone formulation and is administered as a bolus dose and the bolus dose is administered in less than 10 minutes and the $C_{max}$ occurs within 1 hour of completion of administration.

The disclosure includes embodiments in which the injectable neurosteroid formulation is a ganaxolone formulation is administered as a single bolus dose and the single bolus dose comprises from about 0.1 mg/kg to about 20 mg/kg ganaxolone. Or, optionally the single bolus dose comprises from about 0.5 mg/kg to about 15 mg/kg ganaxolone, or about 0.5 mg/kg to about 10 mg/kg ganaxolone, or from about 1 mg/kg to about 30 mg/kg ganaxolone.

The disclosure includes embodiments in which multiple bolus doses of the injectable neurosteroid formulation are administered to the patient. In certain embodiments the multiple bolus doses are given over 1 to 10 days at intervals of 1 to 24 hours. In certain embodiments the injectable neurosteroid formulation is a ganaxolone formulation and each bolus dose provides a sufficient amount of ganaxolone to produce a plasma $C_{max}$ of ganaxolone of about 20 ng/mL to about 1000 ng/mL in the patient. In certain embodiments the interval between bolus doses is from about 10 to about 24 hours and once an initial $C_{max}$ is reached the plasma concentration of ganaxolone is not below 20 ng/mL at any time between bolus doses. In certain embodiments the interval between bolus doses is 20 to 24 hours and once an initial $C_{max}$ is reached and the concentration of ganaxolone in the patient's plasma does not fall below 25% of the initial $C_{max}$. In certain embodiment each bolus dose comprises about 0.1 mg/kg to about 20 mg/kg ganaxolone. Or, optionally the single bolus dose comprises from about 0.5 mg/kg to about 15 mg/kg ganaxolone, or about 0.5 mg/kg to about 10 mg/kg ganaxolone, or from about 1 mg/kg to about 30 mg/kg ganaxolone.

In certain embodiments the method comprises administering an infusion of the injectable neurosteroid formulation to the patient, with or without an initial bolus dose. In certain embodiments the infusion is administered for 1 to 10 consecutive days at a rate of 0.5 to 10 mg/kg/hr without an initial bolus dose.

In certain embodiments the injectable neurosteroid formulation is a ganaxolone formulation and the method comprises administering an initial bolus dose of the ganaxolone formulation comprising from about 0.1 mg/kg to about 20 mg/kg ganaxolone, followed within 24 hours by administration of an infusion of the ganaxolone formulation for 1 to 10 consecutive days at a rate of 0.5 to 10 mg/kg/hr.

In certain embodiments the injectable neurosteroid formulation is a ganaxolone formulation and the method comprises administering an initial bolus dose of the formulation followed by an infusion dose, wherein the initial bolus dose provides a sufficient amount of ganaxolone to provide an initial plasma $C_{max}$ of ganaxolone of about 20 ng/mL to about 1000 ng/mL in the patient and the concentration of ganaxolone in the patient's plasma does not fall below 25% of the initial $C_{max}$ until after the subsequent infusion dosing is concluded. The disclosure includes a method of treating postpartum depression in which the infusion provides a plasma $C_{max}$ of ganaxolone of 60 ng/ml. The disclosure also includes a method of treating postpartum depression in which the infusion provides a steady state plasma concentration of 20 ng/ml to 100 ng/ml, or 40 ng/ml to 80 ng/ml, or at least 60 ng/ml.

In certain embodiments the injectable neurosteroid formulation is a ganaxolone formulation and the method comprises administering an initial bolus dose of the ganaxolone formulation, wherein the initial bolus dose provides a sufficient amount of ganaxolone to provide an initial plasma $C_{max}$ of ganaxolone of about 20 ng/mL to about 1000 ng/mL in the patient, the patient is then administered an infusion of the ganaxolone formulation at a constant dose sufficient to provide a concentration of ganaxolone in the patient's plasma of at least 40% of $C_{max}$, followed by an infusion of ganaxolone at a gradually reducing dose so that the concentration of ganaxolone in the patient's plasma is less than 20% of $C_{max}$ when the infusion is concluded.

Combination Treatment

The disclosure includes embodiments in which the neurosteroid is the only active agent and embodiments in which ganaxolone is administered in combination with one or more additional active agents. When used in combination with an additional active agent ganaxolone and the additional active agent may be combined in the same formulation or may be administered separately. Ganaxolone may be administered while the additional active agent is being administered (concurrent administration) or may be administered before or after the additional active agent is administered (sequential administration).

The disclosure includes methods of treating delirium tremens in which the additional active agent is an anticonvulsant or an anxiolytic. Anticonvulsants and anxiolytics include $GABA_A$ receptor modulators, sodium channel blocker, GAT-1 GABA transporter modulators, GABA transaminase modulators, voltage-gated calcium channel blockers, glutamate receptor modulators, and peroxisome proliferator-activated alpha modulators.

The disclosure includes methods of treating delirium tremens in which the patient is given an anesthetic or sedative in combination with ganaxolone. The anesthetic or sedative may be administered at a concentration sufficient to cause the patient to lose consciousness, such as a concentration sufficient to medically induce coma or a concentration effective to induce general anesthesia. Or the anesthetic or sedative may be given at a lower dose effective for slight sedation, but not sufficient to induce a loss of consciousness.

A medically induced coma occurs when a patient is administered a dose of an anesthetic, such as propofol, pentobarbital or thiopental, to cause a temporary coma or a deep state of unconsciousness. General anesthesia is a treatment with certain medications to cause unconsciousness sufficient to be unaware of pain during surgery. Drugs used for medically induced coma or general anesthesia include inhalational anesthetics and intravenous anesthetics which include barbiturate and non-barbiturate anesthetics.

Inhalational anesthetics include desflurane, enflurane, ethyl chloride, halothane, isoflurane, methoxyflurane, sevoflurane, and trichloroethylene.

Intravenous, non-barbiturate anesthetics include atracurium, cisatracurium, etodimidate, ketamine, propofol, and rocuronium, Barbiturates include amobarbital, methohexital, pentobarbital, phenobarbital, secobarbital, thiamylal, and thiopental.

Benzodiazepines are used both as anticonvulsants, anxiolytics and anesthetics. Benzodiazepines useful as anaesthetics include diazepam, flunitrazepam, lorazepam, and midazolam.

The disclosure includes administering propofol to induce anesthesia in combination with ganaxolone. Propofol is administered at a dose range or dosage range of 0.5- 50 mg/kg. Anesthesia is induced with an initial bolus of 10-50 mg/kg followed by additional intermittent boluses or 10-50 mg/kg to maintain anesthesia. Anesthesia may also be maintained by an infusion of 3-18 mg/kg/min propofol.

The disclosure includes administering pentobarbital sodium by intravenous or intramuscular injection to induce anesthesia in combination with ganaxolone. Pentobarbital may be administered to adults as a single 100-500 mg, or 100-200 mg intramuscular or intravenous injection, or to pediatric patients as a single 2 to 6 mg/kg IM or IV injection. Pentobarbital may be administered at a high dose to induce coma in a delirium tremens patient and ganaxolone may then be given in combination with the pentobarbital to treat refractory seizures of delirium tremens. Pentobarbital doses used to induce coma include, a loading dose of 5 to 15 mg/kg or 10 to 35 mg/kg, given over 1-2 hours followed by a maintenance dose of 1 mg/kg/hr to 5 mg/kg/hr for 12 to 48 hours and tapering by 0.25 to 0.5 mg/kg/hr every 12 hours once seizures have stopped.

The disclosure includes administering thiopental sodium in combination with ganaxolone. Thiopental can be administered as a 3 to 5 mg/kg bolus followed by additional boluses of 1 to 2 mg/kg every 3 to 5 minutes until seizures have stopped, to a maximum total dose of 10 mg/kg. After the 10 mg/kg maximum bolus dose of thiopental has been reached, thiopental can be infused at 3 to 5 mg/kg/hr.

The disclosure includes administering midazolam in combination with ganaxolone. Midazolam can be administered as a 0.5 mg/kg to 5 mg/kg loading dose, followed by a 1 to 5 microgram/kg/hour infusion.

In each embodiment in which an additional active agent is administered to induce coma, anesthesia, or sedation, ganaxolone is administered as an injectable neurosteroid formulation and is administered simultaneously or sequentially with the additional active agent and is administered according to any of the dosing schedules set forth herein for ganaxolone administration.

The injectable neurosteroid ganaxolone formulation of this disclosure may be administered to a delirium tremens patient with another active agent. Active agents for use in include a number of drug classes and overlap to a certain extent with the coma-inducing, anesthetic, and sedative drugs that may be used in combination with ganaxolone. Active agents that may be used in combination with the injectable neurosteroid formulation of this disclosure include aldehydes, such as paraldehyde; aromatic allylic alcohols, such as stiripentol; barbiturates, including those listed above, as well as methylphenobarbital and barbexaclone; benzodiazepines include alprazolam, bretazenil, bromazepam, brotizolam, chloridazepoxide, cinolazepam, clonazepam, chorazepate, clopazam, clotiazepam, cloxazolam, delorazepam, diazepam, estazolam, etizolam, ethyl loflazepate, flunitrazepam, flurazepam, flutoprazepam, halazepam, ketazolam, loprazolam, lorazepam, lormetazepam, medazepam, midazolam, nimetazepam, nitrazepam, nordazepam, oxazepam, phenenazepam, pinazepam, prazepam, premazepam, pyrazolam, quazepam, temazepam, tatrazepam, and triazolam; bromides, such as as potassium bromide; carboxamides, such carbamazepine, oxcarbazepine, and eslicarbazepine acetate; fatty acids, such as valproic acid, sodium valproate and divalproex sodium; fructose derrivatives, such as toprimate; GABA analogs such as gabapentin and pregabalin, hydantoins, such as ethotoin, phenytoin, mephenytoin, and fosphenytoin; other neurosteroids, such as allopregnanolone, oxasolidinediones, such as paramethadione, trimethadione, and ethadione, propionates such as beclamide; pyrimidinediones such as primidone, pyrrolidines such as brivaracetam, levetiracetam, and seletracetam, succinimides, such as ethosuximide, pensuximide, and mesuximide; sulfonamides such as acetazoloamide sultiame, methazolamide, and zonisamide; triazines such as lamotrigine, ureas such as pheneturide and phenacemide; NMDA antagonists such as felbamate, and valproylamides such as valpromide and valnoctamide; and perampanel.

This disclosure includes methods of treating postpartum depression, PMDD, or postmenopausal depression, in which the neurosteroid, e.g. ganaxalone is administered together with one or more non-neurosteroidal antidepressant. For example the non-neurosteroidal anti-depressant may be a selective serotonin reuptake inhibitor such as citalopram, escitalopram, femoxetine, fluoxetine, fluvoxamine, paroxetine, sertraline, or zimeldine; a serotonin partial agonist such as pindolol, gepirone, or flesinoxan; a selective serotonin norepinephrine reuptake such as duloxetine, venlafaxine, desvenlafaxine, milnacipran, or clovoxamine; a norepephrine reuptake inhibitor such as atomoxetine and reboxetine; a serotonin-2 antagonist reuptake inhibitor such as trazodone; and alpha-2 antagonist/serotonin 5HT2-3 receptor antagonist such as mirtazapine; a norepinephrine dopamine reuptake inhibitors such as bupropion, or a tricyclic antidepressants include, but are not limited to, doxepin, amitriptyline, amoxapine, clomipramine, desipramine, doxepin, imipramine, maprotiline, nortriptyline, protriptyline, and trimipramine.

The disclosure also includes methods of treating PPD in women with bipolar disorder. Methods of treating bipolar depression or PPD in women with bipolar disorder include administering an oral dose of ganaxolone. The total oral daily dose for treating PPD in women with bipolar disorder is from 50 mg to 2000 mg ganaxolone, administered as a single daily dose or twice daily. In other embodiments the total ganaxolone daily dose is 200 mg to 1500 mg, 300 mg to 1200 mg, or 300 mg to 900 mg, or 600 mg, administered in a single daily dose or two doses. In some embodiments ganaxolone is administered together with another active agent used for the treatment of bipolar depression such as lithium, lamotrigine, quetiapine, olanzapine, valproate, carbamazepine, and lurasidone. In certain embodiments a patient suffering from bipolar depression may first be treated with an injectable neurosteroid, such as and intravenous ganaxolone infusion for 1-5 days, and then switched to oral ganaxolone.

Method of treating postpartum depression, PMDD, or postmenopausal depression include administering an injectable neurosteroid formulation, such as an injectable ganaxolone formulation, to the patient as a single bolus dose, multiple bolus doses given over a period of 1 hour to several days, or as an intravenous infusion administered from 6 hours to 96 hours followed by maintenance administration of a ganaxolone oral formulation. Methods of treating postpartum depression include administering an oral dose of ganaxolone daily beginning in the luteal phase of the menstrual cycle, or at day 18-24 of the menstrual cycles until day 2-4 of the menstrual cycle. The total oral daily dose is from 100 mg to 2000 mg ganaxolone, administered as a single daily dose or twice daily. In other embodiments the total ganaxolone daily dose is 200 mg to 1500 mg, 300 mg to 1200 mg, or 300 mg to 900 mg, or 600 mg, administered in a single daily dose or two doses. Ganaxolone oral formulations have been previously disclosed, for example in U.S. Pat. Nos. 9,056,116, 9,029,355, 8,618,087, 8,318,714, 8,022,054, and U.S. Pat. No. 7,858,609, each of which is incorporated by reference for its teachings regarding oral ganaxolone formulations.

Specific Embodiments

In a first embodiment the disclosure provides a method of treating a patient having postpartum depression, premenstrual dysphoric disorder, menopausal depression, or delirium tremens comprising administering an effective amount of an neurosteroid formulation to the patient; wherein the neurosteroid formulation is an ganaxolone formulation.

In an embodiment the ganaxalone formulation is an intravenous formulation.

In an embodiment wherein the intravenous ganaxolone formulation comprises a) water; b) sulfobutyl ether-β-cyclodextrin (CAPTISOL) and ganxalone, wherein the ratio of sulfobutyl ether-β-cyclodextrin to ganaxolone wherein weight to weight (w/w) ratio of sulfobutyl ether-β-cyclodextrin is about 52:1 or greater; and c) a buffer, the formulation having a pH of 6.8 to 7.6. The intravenous ganaxolone formulation of this embodiment may additionally comprise 0.5% to 1.5% weight percent sodium chloride; and 0.5% to 15% weight percent surfactant, wherein the surfactant is selected from the group consisting of a sorbitan ester, a polyoxyethylene sorbitan fatty acid ester, a poloxamer, a cholesterol salt, or a bile salt.

In any of the previous embodiments formulation comprises 0.1 mg/mL to 15 mg/mL ganaxolone and 5.5 mg/mL to 800 mg/ml sulfobutyl ether-β-cyclodextrin.

In any of the previous embodiments the formulation additionally comprises a preservative, and the preservative is benzyl alcohol, chlorbutanol, 2-ethoxyethanol, parabens (including methyl, ethyl, propyl, butyl, and combinations), benzoic acid, sorbic acid, chlorhexidene, phenol. 3-cresol, thimerosal, or a phenylmercurate salt.

The disclosure also provides a method of treating a patient having postpartum depression, premenstrual dysphoric disorder, menopausal depression, or delirium tremens comprising administering an effective amount of an injectable neurosteroid formulation to the patient; wherein the formulation comprises a neurosteroid selected from allopregnanolone, ganaxolone, alphaxalone, alphadolone, hydroxydione, minaxolone, pregnanolone, tetrahydrocorticosterone, and combinations of the foregoing;

a surface stabilizer selected from hydroxyl ethyl starch, dextran, and povidone; and a surfactant.

In certain embodiments in which the formulation comprises a surface stabilizer, the neurosteroid is ganaxolone.

In certain embodiments in which the formulation comprises a surface stabilizer, the neurosteroid is allopregnanolone.

In certain embodiments in which the formulation comprises a surface stabilizer, the surface stabilizer is hydroxyethyl starch.

In certain embodiments in which the formulation comprises a surface stabilizer, the surface stabilizer is sodium cholate, sodium deoxycholate, or sodium cholesterol sulfate.

In certain embodiments in which the formulation comprises a surface stabilizer, wherein the (wt:wt) ratio of the neurosteroid to the surface stabilizer is about 4:1 to about 3:1.

In certain embodiments in which the formulation comprises a surface stabilizer, the nanoparticles have a D50 of 10 nm to 300 nm;

the formulation additionally comprises 0.5% to 1.5% weight percent sodium chloride;

the formulation additionally comprises a buffer and a preservative selected from benzyl alcohol, chlorbutanol, 2-ethoxyethanol, parabens (including methyl, ethyl, propyl, butyl, and combinations), benzoic acid, sorbic acid, chlorhexidene, phenol, 3-cresol, thimerosal, phenylmercurate salt, and combinations of the foregoing.

In any preceding embodiment the patient can be administered 0.1 mg/kg to 200 mg/kg neurosteroid as a single bolus dose. The single bolus dose can be a bolus dose can provide a sufficient amount of ganaxolone to provide a plasma $C_{max}$ of ganaxolone of at least 60 ng/mL in the patient.

In any preceding embodiment the patient can be administered the formulation as an intravenous infusion for 1 hour to 10 consecutive days at a rate of 1 to 10 mg neurosteroid/hr/kg, with or without an initial bolus dose.

In any embodiment in which the neurosteroid is an injectable neurosteroid formulation, the formulation can be administered to the patient as a ganaxolone infusion administered at the rate of 2 mg/hr to 4 mg/hr.

In any preceding embodiment the injectable neurosteroid formulation administered to the patient is a ganaxolone infusion administered at a rate sufficient to provide a steady state plasma concentration of 50 ng/ml to 100 ng/ml. In certain embodiments the ganaxolone infusion is administered at for 36 hrs to 72 hrs.

The disclosure includes a method of treating a patient, wherein the patient is a patient having premenstrual dysphoric disorder and the patient is administered a daily oral dose of ganaxolone of 100 mg to 2000 mg administered from day 18-24 of the patients menstrual cycles until day 2-4 of the patient's menstrual cycle.

The disclosure includes a method of treating a patient, wherein the patient is a patient having menopausal depression and the patient is administered a daily oral dose of ganaxolone of 100 mg to 2000 mg ganaxolone.

The disclosure includes a method of treating a patient, wherein the patient is a patient having postpartum depression, premenstrual dysphoric disorder, or menopausal depression, and the patient is administered the ganaxolone in combination with an SSRI or SNRI antidepressant.

The disclosure includes a method of treating a patient, wherein the patient is a patient having delirium tremens and the patient is administered a ganaxolone intravenous infusion at a rate of 50 mg/hr to 500 mg/hr for 1 to 5 days. In this embodiment the patient may be administered the ganaxolone in combination with an intravenous benzodiazepine infusion.

EXAMPLES

Example 1

Preparation of Injectable Ganaxolone Formulation

Ganaxolone solubility in aqueous CAPTISOL solution was first determined by constructing a phase solubility diagram. Excess ganaxolone was shaken in aqueous CAPTISOL solutions of known concentrations for 42 hours to reach equilibrium. The ganaxolone solution was filtered into HPLC vials through 0.45 μm syringe filters. The filtrates were assayed for ganaxolone concentration by HPLC. The results are summarized in Table 1. Moles of ganaxolone in solution against moles of CAPTISOL added were plotted. Ganaxolone solubility in water was found to increase linearly with the addition of CAPTISOL indicating the formation of 1:1 complex between ganaxolone and CAPTISOL. A plot of weight (mg) of ganaxolone in solution against weight (mg) of CAPTISOL added (FIG. 1), shows the weight:weight ratio of CAPTISOL to ganaxolone required for ganaxolone solubilization at equilibrium to be approximately 52:1.

TABLE 1

| No. | CAPTISOL conc. (mg/mL) | CAPTISOL conc. (M) | Ganaxolone conc. by HPLC (mg/mL) | Ganaxolone conc. (M) |
|---|---|---|---|---|
| 1 | 400 | 0.185 | 7.68 | 0.0231 |
| 2 | 200 | 0.0925 | 3.63 | 0.0109 |
| 3 | 100 | 0.0462 | 1.86 | 0.0056 |
| 4 | 50 | 0.0231 | 0.88 | 0.0027 |
| 5 | 25 | 0.0116 | 0.43 | 0.0013 |
| 6 | 0 | 0 | Not detectable | 0 |

To prepare injectable solutions, excess ganaxolone is added to an aqueous 400 mg/mL CAPTISOL solution. The solution is shaken at least overnight and filtered through a 0.45 micron filter. Ganaxolone concentration of the filtered solution is determined by HPLC. The ganaxolone/CAPTISOL solution (7.68 mg/mL in 400 mg/mL aqueous CAPTISOL) is diluted in saline to obtain 3.84 mg/mL, 0.77 mg/mL and 0.39 mg/mL ganaxolone solutions in 0.9% saline. All solutions were clear and free from any visible precipitation. The ganaxolone solutions remained free of any visible precipitation after freezing and thawing.

Example 2

Preparation of Injectable Ganaxolone-CAPTISOL Solution (5 MG/ML)

Ganaxolone (0.50 g) was first mixed manually using a spatula with a small amount (approximately 20 mL) of 30% w/v CAPTISOL solution in sterile water for injection to form a uniform paste. Additional amount (approximately 40 mL) of 30% w/v CAPTISOL solution was then added to obtain a slurry. The suspension was stirred using a magnetic stir bar for 20 minutes. It was sonicated using a probe sonicator for 2 hours. While sonicating, an additional 30% w/v CAPTISOL solution was added until total amount of the CAPTISOL solution reached 99.58 mL. The stirred formulation was then heated at 68.5° C. for about 2.5 hours to obtain a solution. Heat was removed and the solution was stirred at room temperature for approximately 2 hours. Volume lost due to evaporation was replenished with water. The clear solution was sterile filtered through 0.2 μm Nylon membrane filter.

Example 3

Buffered Ganaxolone-CAPTISOL Solutions

Monobasic potassium phosphate (19.6 mg) and dibasic sodium phosphate heptahydrate (93.3 mg) were added to 3 mg/mL ganaxolone solution in 30% Captisol (20 mL) with an initial pH 4.53. The mixture was sonicated for 1 minute to obtain a clear solution having pH 6.95. About 10 mL of this solution was maintained at 80° C. with magnetic stirring alongside the unbuffered control in closed glass vials. The remaining 10 mL of the sample was kept at 5 ° C. as control. Aliquots were taken at 67 hours and 5 days. The samples were analyzed by HPLC and results are shown in Table 2.

TABLE 2

Stability of unbuffered and phosphate buffered ganaxolone/Captisol solution after 5 days at 80° C.
Stability of Buffered Ganaxolone Solutions

| | 5 days at 5° C. | | 67 h at 80° C. | | 5 days at 80° C. | |
|---|---|---|---|---|---|---|
| Degradation product | Unbuffered | Phosphate Buffered PH 6.95 | Unbuffered | Phosphate buffered pH 6.95 | Unbuffered | Phosphate Buffered PH 6.95 |
| 3-Epimer of ganaxolone | ND | ND | 0.64% | ND | 1.89% | 0.03% |
| 17-Epimer of ganaxolone | ND | ND | 0.13% | 0.07% | 0.39% | 0.13% |

ND, Not detected

Example 4

Injectable Ganaxolone- 30% CAPTISOL Solution Containing Polysorbate 80

500 μl of 10% aqueous Polysorbate 80 solution in a 20 ml scintillation vial were combined with powdered ganaxolone (50 mg). The mixture was stirred to wet the ganaxolone. Solid Captisol (3.2 g), sufficient to form a 30% Captisol solution, was then added to the vial and the vial contents were mixed. Deionized water (8.0 g) was then added and the mixture was vigorously stirred at room temperature overnight to obtain a hazy solution. An aliquot was filtered through 0.2 µm syringe filter and ganaxolone concentration was assayed by HPLC to be 4.28 mg/ml.

The following injectable ganaxolone-30% Captisol solutions were prepared by the methods of this example.

(a) Ganaxolone-30% Captisol solution containing ethanol.

Ganaxolone was vigorously stirred in 30% Captisol in the presence of 10% v/v ethanol overnight to obtain a 3.16 mg/ml ganaxolone solution.

(b) Ganaxolone-30% Captisol solution containing glycerin

Ganaxolone was vigorously stirred in 30% Captisol in the presence of 10% v/v glycerin overnight to obtain a 3.45 mg/ml ganaxolone solution.

(c) Ganaxolone-30% Captisol solution containing propylene glycol

Ganaxolone was vigorously stirred in 30% Captisol in the presence of 10% v/v propylene glycol overnight to obtain a 2.53 mg/ ml ganaxolone solution.

Example 5

Preparation of ganaxolone/30% CAPTISOL Solution by Prior Dry Mixing of Ganaxolone and CAPTISOL Powdered ganaxolone (125 mg) was charged into 100 ml beaker. Captisol powder (7.9 g) was then added to the beaker. The mixture was mixed by stirring with a magnetic stir bar for 5 minutes. Deionized water (20.1 g) was weighed into a plastic cup. About half of the water was added into the beaker and the contents were vigorously stirred for 30 minutes to obtain a homogeneous mixture. The remaining water was added and the beaker was covered with paraffin film. The contents were stirred vigorously at room temperature overnight to obtain a 4.61 mg/ ml ganaxolone solution. After 90 hours of stirring, the ganaxolone concentration remained unchanged.

Example 6

Preparation of Ganaxolone Nanosuspension (10% WT) Via Wet Bead Milling

An aqueous slurry (250 g) containing ganaxolone (25g), hydroxyethyl starch (7.5g), sodium deoxycholate (0.5g) and 30% simethicone (1 drop) was milled using a Netzsch Mill (Minicer) with 0.3 mm YTZ beads (Yttrium stabilized grinding media, Tosoh Corporation, Japan, $ZrO_2+HfO_2$ (95 wt % (weight %)), Y2O2 (5 wt %)). Two additional portions of solid sodium deoxycholate (0.5g each) were added at 100 and 130 minutes after milling had started. The particle size of the milled slurry was measured using a Horiba LA-910 laser diffraction particle size analyzer. After 170 minutes of milling, D50 was 192 nm (188 nm after 1 min sonication). At this point, milling was stopped and the milled slurry was kept at room temperature overnight. The next morning, milling was resumed until the total milling time had reached 320 minutes, at which point D50 was 167 nm (169 nm after 1 minute sonication). The D50 particle size was measured on a Horiba 910 Laser Light Scattering instrument.

Example 7

Preparation of Ganaxolone Nanosuspension (20% WT) Via Wet Bead Milling

An aqueous slurry (250 g) containing ganaxolone (50 g), hydroxyethyl starch (15 g), sodium deoxycholate (3 g) and 30% simethicone (0.15 g) was milled using a Netzsch mill (Minicer) with 0.3 mm YTZ beads for 240 minutes. The D50 of the milled slurry was 189 nm (185 nm after 1 minute sonication).

Example 8

Preparation of Ganaxolone Nanosuspension (20% WT) Via Wet Bead Milling Using 0.2 mm YTZ Beads An aqueous ganaxolone slurry having the same composition as described in Example 2 was milled using a Netzsch mill (Minicer) with 0.2 mm YTZ beads for 245 minutes. The D50 was 172 nm (167 nm after 1 minute sonication).

Example 9

Preparation of Ganaxolone Nanosuspension Containing Dextran 70 Via Wet Bead Milling An aqueous ganaxolone slurry (250 g) containing ganaxolone (25 g), dextran 70 (7.5 g), sodium deoxycholate (1.5 g), and 30% simethicone (0.075 g) was milled using a Netzsch mill (Minicer) with 0.2 mm YTZ beads for 195 minutes to obtain a ganaxolone nanosuspension with D50 of 159 nm (158 nm after 1 minute sonication). Prolonged milling caused particle size to increase to 215 nm (212 nm after 1 minute sonication).

Example 10

Preparation of Ganaxolone Nanosuspension Containing 10% Hydroxyethyl Starch

An aqueous ganaxolone suspension (250 g) containing ganaxolone (25 g), hydroxyethyl starch (25 g), sodium deoxycholate (3 g) and 30% simethicone (0.15 g) was milled using a Netzsch mill (Minicer) with 0.2 mm YTZ beads for 150 minutes to obtain a ganaxolone nanosuspension with D50 value of 139 nm (140 nm after 1 minute sonication).

Example 11

Dilution of Ganaxolone Nanosuspension Concentrate and Sterile Filtration Through 0.2 Micron Filter The ganaxolone nanosuspension of Example 10 was diluted 5-fold with HPLC grade water to obtain a nanosuspension containing about 20 mg/mL ganaxolone. This suspension was filtered through a 0.2 µm syringe filter (Cellulose acetate, 25 mm, 0.2 µm, product #: 13-250020-25 PK, Scientific Strategies). The particle size of the filtered ganaxolone suspension was measured and found to be: D50, 143 nm (143 nm after 1 minute sonication); D90, 219 nm; D95, 289 nm.

Example 12

Ganaxolone Nanosuspension Containing Poloxamer 188

A KDL Bachofen Mill was configured with the batch chamber attachment (approx. 350 ml) and the 96 mm polyurethane rotor attached to the shaft. Next, 265 ml of 0.3 mm ytria-zirconia beads were added dry to the chamber, followed by 176.7 gm of the Ganaxolone (GNX) slurry. Slowly, over 15 minutes, the ganaxolone slurry was added to the milling media containing Pluronic F-68 (Poloxamer 188) with sustained stirring. The mixture was stirred slowly overnight. The slurry was milled at Speed 1 (1500 rpm) with intermittent measurement of particle size. After 90 minutes, the D50 particle size was determined to be 378 nm. The D50 measurement was measured on a Horiba 910 Laser Light Scattering instrument.

| Milling Media | |
|---|---|
| Pluronic F-68 | 27.0 g |
| Sodium deoxycholate | 2.7 g |
| Simethicone emulsion 30% | 0.2 g |
| Water (DI) | to 200 g |
| Ganaxolone Slurry | |
| Ganaxolone | 50 g |
| Milling Media | 150 g |
| Final Milling Composition (wt %) | |
| Ganaxolone | 25% |
| Pluronic F-68 | 10% |
| Deoxycholate | 1% |

Example 13

Ganaxolone Nanosuspension Containing Poloxamer 188, 0.1 MM Beads

The KDL Bachofen mill was configured with the batch chamber attachment (approx. 350 ml) and the 96 mm polyurethane rotor attached to the shaft. Next, 300 ml of 0.1 mm ytria-zirconia beads were added dry to the chamber, followed by 134.6 gm Ganaxolone (GNX) slurry having the composition given in preceding Example 9. The slurry was milled for 60 minutes and the D50 particle size was measured after 20, 40, 60 minutes of milling.

| Time (min) | Particle size, μm | After sonication, μm |
|---|---|---|
| 20 | 0.182 | 0.183 |
| 40 | 0.164 | 0.165 |
| 60 | 0.162 | |

Example 14

Ganaxolone Nanosuspension Containing 12.5% Poloxamer 188 and Dextran

The KDL Bachofen mill was configured with the batch chamber attachment (approx. 350 ml) and the 96 mm polyurethane rotor attached to the shaft. Next, 300 ml of 0.1 mm yttria-zirconia beads were added dry to the chamber, followed by 176.5 gm of the Ganaxolone (GNX) milling suspension. The ganaxolone milling suspension was prepared by combining the dextran, Pluronic F-68, sodium deoxcholate, and simethicone emulsion ingredients with stirring, and then adding the ganaxolone last with stirring. The suspension stirred for 1.5 hr. The suspension (176.5 gm was added to the batch chamber and the mill started at Speed setting 1. The slurry was milled for 60 minutes and the D50 particle size was measured after 20, 40, 50, and 60 minutes of milling.

| Ganaxolone Milling Suspension | |
|---|---|
| Dextran (40K mol. wt.) | 10.0 g |
| Pluronic F-68 | 25.0 g |
| Sodium deoxcholate | 0.5 g |
| Simethicone emulsion 30% | 0.2 g |
| Ganaxolone | 20.0 g |
| Water (DI) | to 200 g |
| Final Milling Composition (wt %) | |
| Ganaxolone | 20% |
| Dextran | 5% |
| Pluronic F-68 | 25% |
| Sodium Deoxycholate | 0.25% |

| Time (min) | Particle size, μm | After sonication, μm |
|---|---|---|
| 20 | 0.221 | 0.219 |
| 40 | 0.173 | — |
| 50 | 0.166 | 0.168 |
| 60 | 0.164 | — |

The milled suspension above (64.4 gm) was treated with methyl paraben Na (0.074 gm and citric acid (0.027 gm) and the particle size monitored over time.

| Day | Particle size, μm |
|---|---|
| 0 | 0.191 |
| 2 | 0.194 |
| 5 | 0.313 |
| 6 | 0.317 |

Example 15

Treatment of Postpartum Depression With Injectable Ganaxolone CAPTISOL Formulation An injectable ganaxolone/ Captisol formulation of example 4 containing Polysorbate 80 was used in this study. An injectable ganaxolone nanoparticle formulation containing a polymeric stabilizer, an ionic surfactant such as sodium deoxycholoate, sucrose, and a buffer may also be used. Subjects are 18-45 year old females who experienced a Major Depressive Episode in the postpartum period beginning during the last trimester or within the first 4 weeks following delivery, exhibit a HAM-D-17 score of 26 or greater, a Clinical Global Impression of Severity (CGI-S) score of 5 or greater; and were less than 6 months postpartum. All subjects have ceased lactating, or if still lactating have already fully and permanently weaned their infant; or if still actively breastfeeding, patients agree to cease giving breast milk to their infant prior to study entry. Five subjects are administered the ganaxolone/ Captisol formulation as an intravenous infusion at a rate of 3 mg/hr, which is considered sufficient to produce a steady state ganaxolone plasma concentration of 60 ng/ml. The infusion is administered for 60 hours. The control group includes five subject who are administered a placebo infusion of physiological saline, also for 60 hours. Initiation of the infusion is considered T zero ($T_0$). A depression symptom rating scale, either the HAM-D-17 or MADRS is administered to all subjects periodically from $T_0$ to $T_{72}$ (within 72 hours after starting the infusion) and then administered at least once during the 30 day post infusion follow-up period.

Example 16

Treatment of Premenstrual Dysphoric Disorder

The following study is a randomized, double-blind cross over trial. To be eligible participants must be between the ages of 21-46 and have regular menstrual cycles. Eligible participants must meet the DSM 5 criteria for PMDD. Eligible participants must have a definitive PMDD diagnosis and also meet the daily rating severity of Problems (DRSP) criteria showing menstrual cyclicity of symptoms (see below). Participants will be required to maintain a daily menstrual calendar and must be able and willing to use a non-hormonal method of birth control.

Eligible participants will be randomized to either ganaxolone or placebo for 2 menstrual cycles and then switched to the other condition for 2 menstrual cycles. They will have a final assessment after they have completed charting and 4 cycles of double blind treatment. Treatment will be initiated in the middle of the luteal phase of the menstrual cycle and participants will be asked to stop taking pills short after the onset of menses.

At the initial visit the patient will be administered the Structured Clinical Interview for DSM-5. Eligible participants will have blood collected for a chemistry profile and a complete blood count and will provide urine for a pregnancy and drug use test. The following efficacy measures will be obtained: luteal phase symptom severity, with the luteal phase defined as the 7 days prior to the onset of menses for this and subsequent visits, using the Premenstrual Tension Scale (PMTS), the Inventory of Depressive Symptomatology (IDS-C) and the Clinical Global Impressions (CGI)-Severity scale. Health-related quality of life and functional impairment during the 7 days prior to the onset of menses will be evaluated at this visit and every 2 to 4 months using the Quality of Life, Enjoyment and Satisfaction Questionnaire (Q-LES-Q).

This study is designed to show that replacement of declining neurosteroid levels diminishes the symptoms of PMDD. Therefore each participant should commence treatment around the progesterone peak during the luteal phase of the menstrual cycle (~Day 22) and continue treatment until the peak symptomatic period that ends at Day 3 of the subsequent menstrual cycle. Each participant will begin monitoring ovulation the Day 10 of her menstrual cycle using an ovulation monitoring kit, with day 1 being the first day of menses and continue monitoring until the indicator shows that ovulation is imminent. The participant will start pills days 10 days after the indicator is positive for ovulation. Women will take pills from bottles that have a medication event monitoring cap (MEM cap) that tracks when the bottle is opened and hence capsules taken.

Dosing. Study participants will take oral ganaxolone on the following schedule.

| | Day of Menstrual Cycle | | |
|---|---|---|---|
| | Day 22-26 | Day 27-Day 2 | Day 3-4 |
| AM | 1 cap | 2 caps | 1 caps |
| PM | 1 cap | 2 caps | 1 caps |
| Total Dose | 600 mgs | 1200 mgs | 600 mgs |

Treatment visits 2-4. Subjects will be seen for follow-up visits approximately 1-3 days after onset of menses in order to assess all luteal phase symptoms, side effects and possible discontinuation symptoms. Cross over to the other condition will occur at Visit 3. Rating scales will be administered (PMTS, CGI-Severity and Improvement Scales, IDS-C).

Example 17

Treatment of Postmenopausal Depression

The following study is a randomized, double-blind trial. To be eligible participants must be females over the age of 44 and have ceased having menses for at least one year. Eligible participants must meet the DSM 5 criteria for MDD.

Eligible participants will be randomized to either treatment with ganaxolone or placebo Participants will be administered a depression symptoms rating scale, either the HAM-D-17 or MADRS one week prior to the study, at study commencement, and each week during the study. Study participants in the experimental group will receive 2 doses oral ganaxolone of 300 mg each, twice daily. Allopregnanolone levels of all subjects will be measured throughout the study. The primary end-point in this study will be change from baseline in HAM-D-17 or MADRS scores between the placebo and ganaxolone arms. The duration of treatment will be 12-weeks.

Example 18

Treatment of Alcohol-Withdrawal Delirium Tremens

Patients experiencing acute alcohol-withdrawal delirium tremens who remain delirious and agitated despite treatment with standard of care benzodiazepine regimen will be randomized to receive an add-on intravenous ganaxolone infusion or placebo infusion. The intravenous ganaxolone dose will be from 50 mg/hr to 500 mg/hr and will be administered for 1 to 5 days. Patients will be monitored for agitation, seizures, use of additional rescue benzodiazepines, vital signs and clearing of delirium. Patient's vital signs will be monitored continuously during treatment. The study will be conducted in a medical inpatient unit or ICU.

What is claimed is:

1. A method of treating postpartum depression, premenstrual dysphoric disorder, menopausal depression, or delirium tremens comprising administering an effective amount of an neurosteroid formulation to a patient in need thereof; wherein the neurosteroid formulation is an ganaxolone formulation comprising
   a) water;
   b) sulfobutyl ether-β-cyclodextrin (CAPTISOL) and ganaxalone, wherein the ratio of sulfobutyl ether-β-cyclodextrin to ganaxolone wherein weight to weight (w/w) ratio of sulfobutyl ether-β-cyclodextrin is about 52:1 or greater; and
   c) a buffer, the formulation having a pH of 6.8 to 7.6.

2. The method of claim 1 wherein the ganaxalone formulation is an intravenous formulation.

3. The method of claim 1, wherein ulation comprises 0.1 mg/mL to 15 mg/mL ganaxolone and 5.5 mg/ mL to 800 mg/ml sulfobutyl ether-β-cyclodextrin.

4. The method of claim 2, wherein the patient is administered 0.1 mg/kg to 200 mg/kg neurosteroid as a single bolus dose.

5. The method of claim 4, wherein the single bolus dose provides a sufficient amount of ganaxolone to provide a plasma $C_{max}$ of ganaxolone of at least 60 ng/ mL in the patient.

6. The method of claim 2, wherein the patient is administered the formulation as an intravenous infusion for 1 hour to 10 consecutive days at a rate of 1 to 10 mg neurosteroid/hr/kg, with or without an initial bolus dose.

7. The method of claim 2, wherein the intravenous neurosteroid formulation administered to the patient is a ganaxolone infusion administered at the rate of 2 mg/hr to 4 mg/hr.

8. The method of claim 2, wherein the intravenous neurosteroid formulation administered to the patient is a ganaxolone infusion administered at a rate sufficient to provide a steady state plasma concentration of 50 ng/ml to 100 ng/ml.

9. The method of claim 7, wherein the intravenous neurosteroid formulation is a ganaxolone formulation which is administered at for 36 hrs to 72 hrs.

10. The method of claim 1, wherein the patient is a patient having premenstrual dysphoric disorder and the patient is administered a daily oral dose of ganaxolone of 100 mg to 2000 mg administered from day 18-24 of the patients menstrual cycles until day 2-4 of the patient's menstrual cycle.

11. The method of claim 1, wherein the patient is a patient having menopausal depression and the patient is administered a daily oral dose of ganaxolone of 100 mg to 2000 mg ganaxolone.

12. The method of claim 11, wherein the patient is administered the ganaxolone in combination with an SSRI or SNRI antidepressant.

13. The method of claim 1, wherein the patient is a patient having delirium tremens and the patient is administered a ganaxolone intravenous infusion at a rate of 50 mg/hr to 500 mg/hr for 1 to 5 days.

14. The method of claim 13, wherein the patient is administered the ganaxolone in combination with an intravenous benzodiazepine infusion.

* * * * *